US011060973B2

(12) United States Patent
Liu et al.

(10) Patent No.: US 11,060,973 B2
(45) Date of Patent: Jul. 13, 2021

(54) PLASMON RESONANCE IMAGING APPARATUS HAVING METAL-INSULATOR-METAL NANOCUPS

(71) Applicant: The Board of Trustees of the University of Illinois, Urbana, IL (US)

(72) Inventors: Gang Logan Liu, Champaign, IL (US); Lynford L. Goddard, Champaign, IL (US); Abid Ameen, Chandler, AZ (US); Lisa Anne Plucinski Hackett, Albuquerque, NM (US); Faiza Khawar Dar, Chandler, AZ (US)

(73) Assignee: BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

(21) Appl. No.: 16/408,695

(22) Filed: May 10, 2019

(65) Prior Publication Data

US 2019/0369019 A1    Dec. 5, 2019

Related U.S. Application Data

(60) Provisional application No. 62/669,417, filed on May 10, 2018.

(51) Int. Cl.
*G01N 21/55* (2014.01)
*G01N 21/552* (2014.01)
(Continued)

(52) U.S. Cl.
CPC ..... *G01N 21/554* (2013.01); *G01N 33/54366* (2013.01); *B82B 1/001* (2013.01);
(Continued)

(58) Field of Classification Search
CPC ......... B82Y 40/00; B82Y 15/00; B82Y 30/00; B82Y 5/00; B82Y 10/00; B82Y 20/00; B82Y 25/00; G01N 27/4146; G01N 2021/6439; G01N 21/6428; G01N 33/573; G01N 21/554; G01N 21/648; G01N 27/12; G01N 2800/56; G01N 33/54326; G01N 33/54346; G01N 33/54353; G01N 33/5438; G01N 33/58; G01N 2021/458; G01N 2021/6471; G01N 2021/7726; G01N 2021/7776; G01N 2021/7779; G01N 2021/7789; G01N 21/27; G01N 21/41;
(Continued)

(56) References Cited

U.S. PATENT DOCUMENTS 8,637,346 B1 * 1/2014 Jung ..................... C01B 32/186
                                                            438/99
9,464,985 B2   10/2016 Liu et al.
(Continued)

OTHER PUBLICATIONS

"Spectrometer-Free Plasmonic Biosensing with Metal-Insulator-Metal Nanocup Arrays" Lisa P. Hackett et al. ACS Publications, Published Jan. 30, 2018.*
(Continued)

*Primary Examiner* — Michael P Stafira
(74) *Attorney, Agent, or Firm* — DLA Piper LLP US

(57) ABSTRACT

Provided are plasmon resonance imaging devices having metal-insulator-metal nanocups and methods of use thereof.

18 Claims, 20 Drawing Sheets
(19 of 20 Drawing Sheet(s) Filed in Color)

(51) Int. Cl.
*G01N 33/543* (2006.01)
*B82Y 40/00* (2011.01)
*B82Y 15/00* (2011.01)
*B82B 1/00* (2006.01)
*B82B 3/00* (2006.01)
*B82Y 20/00* (2011.01)

(52) U.S. Cl.
CPC ........... *B82B 3/0014* (2013.01); *B82B 3/0019* (2013.01); *B82Y 15/00* (2013.01); *B82Y 20/00* (2013.01); *B82Y 40/00* (2013.01)

(58) Field of Classification Search
CPC .. G01N 21/553; G01N 21/64; G01N 21/6408; G01N 21/6454; G01N 21/6458; G01N 2/658; G01N 21/7703; G01N 21/7743; G01N 21/7746; G01N 21/78; G01N 2201/06113; G01N 2201/062; G01N 2201/0638; G01N 2333/31; G01N 2333/42; G01N 2333/4724; G01N 2333/70596; G01N 2333/726; G01N 2333/82; G01N 2333/974; G01N 23/06; G01N 2458/00; G01N 2500/02; G01N 2500/10; G01N 27/00; G01N 27/3278; G01N 27/4035; G01N 27/4075; G01N 27/445; G01N 27/4148; G01N 2800/042; G01N 2800/105; G01N 2800/226; G01N 2800/52; G01N 33/5032; G01N 33/505; G01N 33/5091; G01N 33/534; G01N 33/54306; G01N 33/54373; G01N 33/552; G01N 33/553; G01N 33/56911; G01N 33/56916; G01N 33/56938; G01N 33/56961; G01N 33/56966; G01N 33/574; G01N 33/57415; G01N 33/57419; G01N 33/57434; G01N 33/57446; G01N 33/57492; G01N 33/587; G01N 33/60; G01N 33/74; G01N 35/0098; G01N 27/4145; G01N 30/92; G01N 33/54366; G01N 33/54393; G01N 2021/6432; G01N 21/658; G01N 27/327; G01N 33/04; G01N 33/146; G01N 33/551; G01N 33/569; G01N 2030/027; G01N 21/65; G01N 27/227; G01N 27/26; G01N 27/414; G01N 30/02; G01N 33/48721; G02B 1/002; G02B 21/0008; G02B 5/12; G02B 5/22; G02B 2006/12061; G02B 2006/12097; G02B 2006/12107; G02B 2006/12138; G02B 21/002; G02B 21/36; G02B 3/0068; G02B 3/0087; G02B 6/1225; G02B 6/136; G01J 2003/425; G01J 3/42; G01J 3/44; G01J 5/10
See application file for complete search history.

(56) References Cited

U.S. PATENT DOCUMENTS

| 2008/0212102 | A1* | 9/2008 | Nuzzo | G01N 21/554 356/445 |
| 2010/0259826 | A1* | 10/2010 | Ji | H01L 31/056 359/599 |
| 2010/0323173 | A1* | 12/2010 | Van Roy | B82Y 30/00 428/208 |
| 2013/0003058 | A1* | 1/2013 | Van Dorpe | G01N 21/658 356/301 |
| 2013/0059232 | A1* | 3/2013 | Jung | H01G 9/2022 429/532 |
| 2014/0206101 | A1* | 7/2014 | Liu | G01N 21/554 436/501 |
| 2015/0037815 | A1* | 2/2015 | Miller | G01N 33/54373 435/7.4 |
| 2018/0003865 | A1* | 1/2018 | Guler | B01J 27/24 |

OTHER PUBLICATIONS

Ameen et al, "Label-free Sensing using 3D plasmonic Nano-Cavity Structures on a Periodic Nanocup Arrays for Biomedical Applications", 2016 MRS Spring Meeting.

Ameen et al, "Plasmonic Sensing of Oncoproteins without Resonance Shift Using 3D Periodic Nanocavity in Nanocup Arrays", Advanced Optical Materials, 1601651, (2017).

Arbabi et al, "Hybrid whispering gallery mode/plasmonic chain ring resonators for biosensing", Applied Physics Letters, vol. 105, No. 231107, (2014).

Babicheva et al, "Plasmonic finite thickness metal-semiconductor-metal waveguide as ultra-compact modulator, Photonics and Nanostructures—Fundamentals and Applications", vol. 11, No. 4, pp. 323-334, (2013).

Cao et al, "Modeling of multi-band circular dichroism using metal/dielectric/metal achiral metamaterials", Optical Materials Express, vol. 4, No. 8, pp. 1526-1534, Jul. 3, 2014.

Chandra et al, "Coupling of plasmonic and optical cavity modes in quasi-three-dimensional plasmonic crystals", Nature Communications, vol. 2, No. 479, Sep. 20, 2011.

Choo et al, "Nanorocusing in a metal-insulator gap plasmon waveguide with a 3-dimensional linear taper", Nature Photonics, vol. 6, No. 12., pp. 837-843, (2012).

Dahlin et al, "Plasmonic Nanopores in Metal-Insulator-Metal Films", Advanced Optical Materials, vol. 2, No. 6, pp. 556-564, Jun. 2014.

Dahlin, "Sensing applications based on plasmonic nanopores: The hole story", Analyst, vol. 140, No. 14, pp. 4748-4759, (2012).

De Angelis et al, "A Hybrid Plasmonic-Photonic Nanodevice for Label-Free Detection of a Few Molecules", Nano Letters, vol. 8, No. 8, pp. 2321-2327, Jun. 6, 2008.

Duan et al, "Enhancement of light absorption of cadmium sulfate nanoparticle at specific wave band by plasmon resonance shifts", Physics B: Low-dimensional Systems and Nanostructures, vol. 43, No. 8, pp. 1475-1480, Jun. 2011.

Hosseini et al, "Optical range microcavities and filters using multiple dielectric layers in multi-insulator-metal structures", Optical Society of America, vol. 24, No. 1, pp. 221-224, Jan. 2007.

Junesch et al, "Optical Properties of Nanohole Arrays in Metal-Dielectric Double Films Prepared by Mask-on-Metal Colloidal Lithography", Acs Nano, vol. 6, No. 11, pp. 10405-10415, Oct. 25, 2012.

Liu et al, "Numerical investigation of finite thickness metal-insulator-metal structure for waveguide-based surface plasmon resonance biosensing", Sensors and Actuators: B Chemical, vol. 148, No. 1, pp. 23-28, Jun. 30, 2010.

Min et al, "High-Q surface-plasmon-polariton whispering gallery microcavity", Nature, vol. 457, No. 7228, pp. 455-458, Jan. 22, 2009.

Shopova et al, "Plasmonic enhancement of a whispering-gallery-mode biosensor for single nanoparticle detection", Applied Physics Letters, vol. 98, No. 243104, Jun. 13, 2011.

Stewart et al, "Quantitative multispectral biosensing and 1D imaging using quasi-3D plasmonic crystals", Proceedings of the National Academy of Sciences of the United States of America. vol. 103, No. 46, pp. 17143-17148, Nov. 14, 2006.

Tabatabei et al, "Tunable 3D Plasmonic Cavity Nanosensors for Surface-enhanced Raman Spectroscopy with Sub Femtomolar Limit of Detection", Acs Photonics, vol. 2, No. 6, pp. 752-759 (2015).

Yu et al, "High Quality Factor Metallodielectric Hybrid Plasmonic-Photonic Crystals", Advanced Functional Materials, vol. 20, No. 12, pp. 1910-1916, Jun. 23, 2010.

(56) References Cited

OTHER PUBLICATIONS

Zia et al, "Geometries and materials for subwavelength surface plasmon modes", J. Opt. Soc. Am. A, vol. 21. No. 12, pp. 2442-2446, Dec. 2004.

\* cited by examiner

PLASMON RESONANCE IMAGING APPARATUS HAVING METAL-INSULATOR-METAL NANOCUPS

PRIORITY

This application claims the benefit of U.S. Ser. No. 62/669,417, filed on May 10, 2018, which is incorporated by reference herein in its entirety.

STATEMENT REGARDING FEDERALLY SPONSORED RESEARCH OR DEVELOPMENT

This invention was made with government support under DE-FG02-07ER46471 awarded by the Department of Energy. The government has certain rights in the invention.

BACKGROUND

Plasmonic sensors are appealing for biosensing applications due to the high sensitivity of the generated evanescent fields to local refractive index (RI) changes. These sensors are currently based on surface plasmon resonance (SPR), extraordinary optical transmission (EOT), localized surface plasmon resonance (LSPR), or a combination of these mechanisms with applications including gas detection, cancer biomarker screening, and cell imaging. EOT plasmonic devices, which primarily rely on the generation of grating-coupled SPR on metallic nanohole arrays, are of particular interest for biosensing applications due to excitation and spectral detection in transmission mode at normal incidence, which simplifies the instrumentation requirements. However, the performance of these devices in terms of limit of detection (LOD) is significantly worse than SPR sensors in the Kretschmann configuration, which has a high angular sensitivity that can exceed 500°/RIU. Current work in plasmonic sensors seeks to match or outperform SPR sensors while simplifying the instrumentation requirements to lead to more widespread applications of these tools.

SUMMARY

An embodiment provides an apparatus, comprising a substrate layer having a top surface and a bottom surface, wherein a plurality of nanocups are defined in the substrate layer, wherein the plurality of nanocups each have at least one sidewall surface and a bottom surface; a first metal layer disposed on the top surface of the substrate layer and a second metal layer disposed on the bottom surface of each of the plurality of nanocups; a first layer of titanium dioxide disposed on the first metal layer disposed on the top surface of the substrate layer and a second layer of titanium dioxide disposed on the second metal layer disposed on the bottom surface of each of the plurality of nanocups; a third metal layer disposed on the first layer of titanium dioxide and a fourth metal layer disposed on the second layer of titanium dioxide; and a layer of titanium dioxide and a plurality of metal nanoparticles on the at least one sidewall surface of the plurality of nanocups.

The nanocups can have a frustoconical shape. The substrate can be a polymer. The substrate can be transparent or translucent. The metal layers and metal nanoparticles can be gold, a mixture of gold and silver, silver, aluminum, copper, platinum, or alloys thereof.

The first, second, third, and fourth metal layers can be about 50 nm to about 100 nm thick, and the first and second titanium dioxide layers can be about 50 nm to about 100 nm thick. The first and second metal layers can be about 80 nm to about 90 nm thick, and the first and second titanium dioxide layers can be about 70 nm to about 80 nm thick. The nanocups can be about 25 nm to about 1,000 nm deep. The nanocups can have a top diameter of about 30 nm to about 300 nm and a bottom diameter of about 25 nm to about 295 nm. The metal nanoparticles can be about 20 nm to about 40 nm in diameter. The substrate can comprise about 20, 50, 100, 500, 1,000 or more nanocups. The plurality of metal nanoparticles can be arranged in a discontinuous manner. The layer of titanium dioxide on the at least one sidewall surface of the plurality of nanocups can be discontinuous.

In an embodiment, an apparatus can have one or more specific binding substances or one or more analytes present on the at least one sidewall, the bottom surface of the nanocups, or both the at least one sidewall and the bottom surface of the nanocups.

In an embodiment, when light is directed to the surface of the device, a superstrate refractive index increase causes a transmission intensity increase at the peak resonance wavelength and there is little to no spectral shift at the peak. The apparatus can comprise spectral regions having no transmission intensity change.

An embodiment provides a system comprising an apparatus as described herein and a white light source or an LED light source.

Another embodiment provides a method of detecting binding of one or more specific binding substances and their respective binding partners using an apparatus described herein, wherein an apparatus has one or more specific binding substances present on the at least one sidewall, the bottom surface of the nanocups, or both the at least one sidewall and the bottom surface of the nanocups. The method comprises applying one or more binding partners to the apparatus; illuminating the apparatus with a light source; and detecting relative intensity; wherein, where the one or more specific binding substances have bound to their respective binding partners, the relative intensity is increased.

Yet another embodiment provides a method of detecting of one or more analytes on an apparatus as described herein, wherein the apparatus has one or more analytes present on the at least one sidewall, the bottom surface of the nanocups, or both the at least one sidewall and the bottom surface of the nanocups. The method comprises applying one or more analytes to the apparatus; illuminating the apparatus with a light source; detecting relative intensity; wherein, where the one or more analytes are present on the at least one sidewall, the bottom surface of the nanocups, or both the at least one sidewall and the bottom surface of the nanocups the relative intensity is increased.

Still another embodiment provides a method of making a nanocup array device. The method comprises depositing a metal layer by e-beam evaporation on a substrate comprising a plurality of nanocups; depositing a titanium dioxide layer by sputtering deposition on the metal layer on the substrate; and depositing another metal layer by e-beam evaporation on the substrate. The method can further comprise immobilizing one or more specific binding substances or analytes to the sidewalls of the nanocups or both the sidewalls and bottoms of the nanocups.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The features, objects and advantages other than those set forth above will become more readily apparent when consideration is given to the detailed description below. Such detailed description makes reference to the following drawings, wherein.

Figure 1:
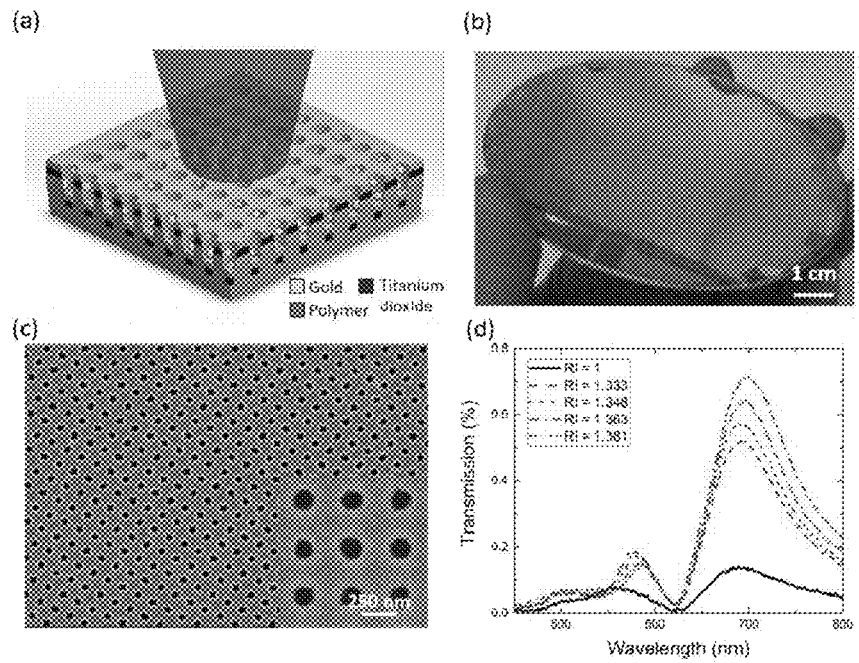
FIG. 1. Fabrication and characterization of Au-titanium dioxide-Au nanocup arrays. (a) Schematic and (b) camera image of wafer-scale MIM nanocup array with 90 nm top and bottom Au layers and 80 nm titanium dioxide cavity layer. The reflected light off the device is diffracted due to the periodic nanocup array. (c) Top-down SEM image of the device. (d) Experimental transmission spectra with increasing RI values. The spectral features show an increase in transmission intensity at the resonance wavelength with spectral locations of no transmission change with RI increase.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims below for interpreting the scope of the invention.

DETAILED DESCRIPTION

Unless defined otherwise, all technical and scientific terms used herein have the same meaning as commonly understood by one of skill in the art to which the systems and methods pertain.

As used herein, the term "and/or" includes any and all combinations of one or more of the associated listed items. As used herein, the singular forms "a," "an," and "the" are intended to include the plural forms as well as the singular forms, unless the context clearly indicates otherwise.

The embodiments illustratively described herein suitably can be practiced in the absence of any element or elements, limitation or limitations that are not specifically disclosed herein. Thus, for example, in each instance herein any of the terms "comprising," "consisting essentially of," and "consisting of" may be replaced with either of the other two terms, while retaining their ordinary meanings.

The term "about" in association with a numerical value means that the numerical value can vary plus or minus by 5% or less of the numerical value. All patents, patent applications, and other scientific or technical writings referred to anywhere herein are incorporated by reference herein in their entirety.

Likewise, many modifications and other embodiments of the apparatus and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Unless defined otherwise, all technical and scientific terms used herein have the same meaning as commonly understood by one of skill in the art to which the systems and methods pertain.

As used herein, the term "and/or" includes any and all combinations of one or more of the associated listed items. As used herein, the singular forms "a," "an," and "the" are intended to include the plural forms as well as the singular forms, unless the context clearly indicates otherwise.

The embodiments illustratively described herein suitably can be practiced in the absence of any element or elements, limitation or limitations that are not specifically disclosed herein. Thus, for example, in each instance herein any of the terms "comprising," "consisting essentially of," and "consisting of" may be replaced with either of the other two terms, while retaining their ordinary meanings.

The term "about" in association with a numerical value means that the numerical value can vary plus or minus by 5% or less of the numerical value. All patents, patent applications, and other scientific or technical writings referred to anywhere herein are incorporated by reference herein in their entirety.

The present disclosure provides a metal-insulator-metal plasmonic nanocup array device (e.g. gold-titanium dioxide-gold metal-insulator-metal plasmonic nanocup array device) for spectrometer-free refractometric sensing with a performance exceeding conventional surface plasmon resonance sensors. The devices show distinct spectral properties such that a superstrate refractive index increase causes a transmission intensity increase at the peak resonance wavelength. There is no spectral shift at this peak and there are spectral regions with no transmission intensity change, which can be used as internal device references. The devices demonstrate a sensitivity exceeding 800 Δ% T/RIU. The high performance and distinct spectral features of metal-insulator-metal plasmonic nanocup arrays make these devices ideal for portable optical sensing systems with minimal instrumentation requirements.

Here, for the first time, multilayered plasmonic devices are provided for spectrometer-free refractometric sensing with a performance exceeding SPR sensors in the Kretschmann configuration. Instrumentation costs, such as for a high-resolution spectrometer, are a limiting factor towards the development of portable optics-based molecular diagnostic systems. While the development of miniaturized, low-cost spectrometers is an active area of research, an alternative approach taken herein is to design a sensor and sensing system that no longer requires spectroscopic measurements, but still maintains a high sensing performance.

Provided are metal-titanium dioxide-metal MIM plasmonic nanocup array for spectrometer-free refractometric sensing based on transmission intensity variations at a fixed resonance wavelength. The sensing mechanism is dominated by the MIM cavity structure, however, the sensitivity and overall transmission of the sensor are determined primarily by the degree of cavity-plasmon coupling, the degree of confinement, and the ability of the chosen materials to generate SPR and LSPR resonances. This sensor design and sensing mechanism are well-suited for the development of compact, portable optical sensors for applications in areas such as drug discovery and diagnostics.

The sensing method comprises transmission resonance intensity measurements occurring in, for example, a metal, titanium dioxide (titanium dioxide), metal plasmonic metal-insulator-metal (MIM) nanocup array. The spectral characteristics of this device show sensitive on-resonance transmission changes with refractometric changes due to plasmon-cavity coupling in the multilayered structure. In addition, spectral locations with no intensity change can be used as internal device references, which is important for reliable transmission measurements outside of a controlled laboratory. FIG. 1(d) demonstrates one of these spectral locations with not intensity change. In FIG. 1(d), there is a spectral location at approximately 625 nm where going from water (refractive index=1.333) to higher refractive index values there is a negligible intensity change compared to the peak intensity change. The intensity value at this spectral location can be used as an internal reference for the device.

While conventional plasmonic sensors can also operate as refractometers based on intensity changes, the LOD for this operating mode is worse than that of angular or spectral methods, and spectral features such as shifts, unreliable intensity changes, and lack of reference points make the data difficult to collect and analyze accurately.

Figure 6:
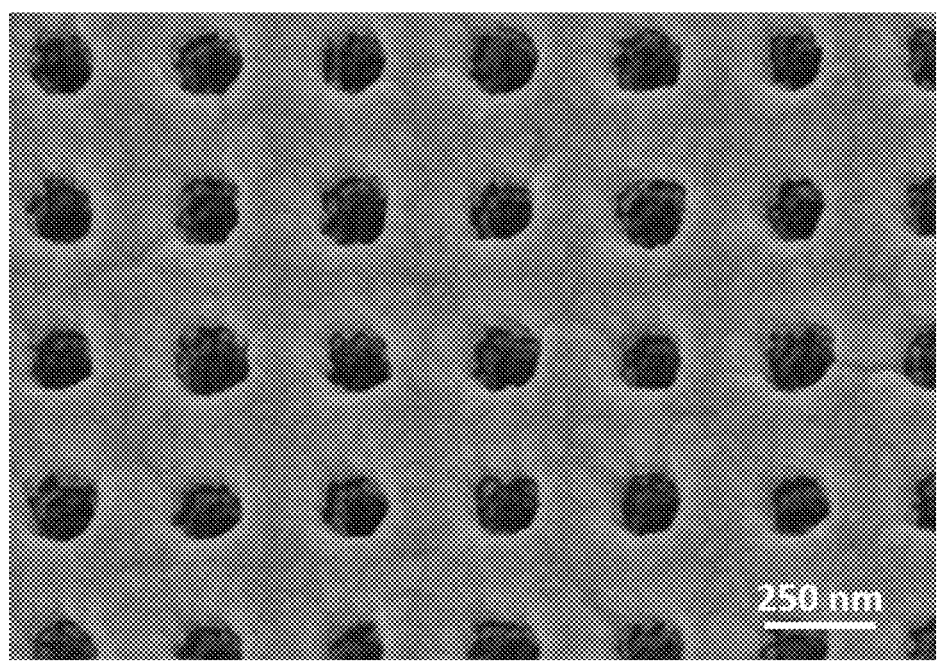
FIG. 6. A tilted SEM image of the MIM nanocup array is shown to visualize the Au nanoparticles that form along the nanocup sidewall.
Figure 17:
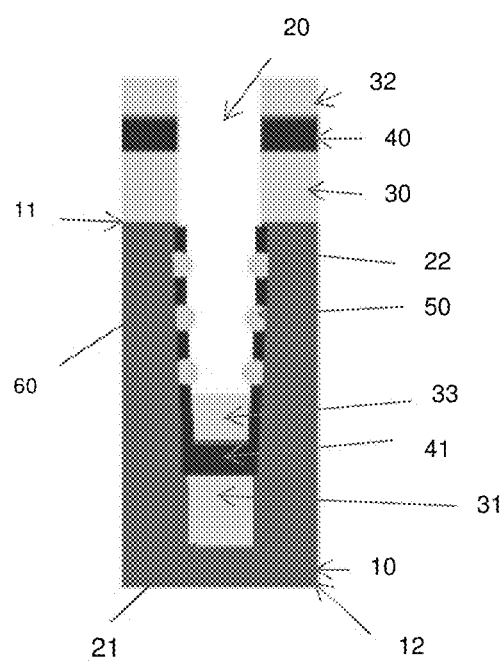
FIG. 17 shows the detail of a nanocup.

In one embodiment, the metal-titanium dioxide-metal nanocup array sensor comprises a nanostructured polymer substrate, fabricated by a wafer-scale nanoreplica molding process, with deposited layers of metal and titanium dioxide. Au can be chosen for the metal layers due to its plasmonic properties, its high field confinement capability due to high reflectivity, and its chemical stability. Titanium dioxide is chosen as the cavity layer material due to its high RI, zero extinction coefficient (k), and good manufacturability. A schematic of the device is shown in FIG. 1a and a camera image is shown in FIG. 1b. A schematic of a nanocup is shown in FIG. 17. In an embodiment, a sensor has a bottom Au layer of 90 nm, titanium dioxide cavity layer of 80 nm, and top Au layer of 90 nm, which is optimized based on simulation and experimental studies that are described later in detail. The camera image shows polychrome color due to the diffraction of the reflected light from the periodic nanocup array structures. A top-down SEM image of the device is shown in FIG. 1c. A well-ordered, periodic array is maintained after the full device fabrication. The inset shows a SEM image at a higher magnification of the top-down view of the individual nanocups. A tilted SEM image of the device, where the sidewall Au nanoparticles are visible, is shown in FIG. 6.

Substrate

An apparatus can comprise a substrate (10) having a top surface (11) and a bottom surface (12). A plurality of nanocups (20) (e.g., 2, 10, 20, 50, 100, 144, 250, 500, 1,000 or more) are defined in the top surface (11) of the substrate (10) and the plurality of nanocups (20) each have at least one sidewall surface (22) and a bottom surface (21).

The nanocups can be about 25 nm to about 1,000 nm deep (e.g., about 25, 50, 75, 100, 200, 300, 400, 500, 600, 700, 800, 900, 1,000 nm or more). The nanocups can have a top diameter of about 25 nm to about 300 nm (e.g. about 25, 30, 50, 75, 100, 125, 150, 175, 200, 225, 250, 275, 295, 300 nm or more) and a bottom diameter of about 25 nm to about 300 nm (e.g. about 25, 30, 50, 75, 100, 125, 150, 175, 200, 225, 250, 275, 295, 300 nm or more). The top diameter of a nanocup can be larger than the bottom diameter.

The nanocups can have a frustoconical shape. The nanocups can have tapered side wall surfaces. In an embodiment the taper angle of a nanocup sidewall (22) is about 60 to about 89.99 degrees (e.g., about 60, 65, 70, 75, 80, 85, 86, 87, 88, 89, 89.5 or 89.99 degrees). If the angle is too shallow, then poor optical confinement and lack of formation of a cavity can result. If the angle is too great, then poor coating of the sidewall can result.

The substrate can be any suitable material including, for example, a polymer. In an embodiment, the substrate is a UV-curable polymer such as acrylated epoxies, acrylated polyesters, or acrylated silicones. A substrate can be transparent or translucent.

Metal-Titanium Dioxide-Metal Layers

A first metal film or layer (30) is present on the top surface of the substrate (11) and a second metal film or layer (31) is present on the bottom surface of each of the plurality of nanocups (20). The metal film or layer can be selected from plasmonic metals such as gold, silver, a mixture of gold and silver, aluminum, copper, platinum, and combinations or alloys thereof. An adhesion layer of, for example, titanium or chrome can be present between the first metal film layer and the top surface of the substrate. An adhesion layer of, for example, titanium or chrome can be present between the second metal film layer and the bottom surface of the nanocups. In an embodiment the first and second metal layers are one metal or alloy (e.g., gold) and the third and fourth metal layers are a different metal or alloy (e.g., silver).

The deposition of the first and second metal film layers, which occurs at the same time, results in a thin coating of the metal or deposition of metal nanoparticles on the sidewalls of the nanocups. This layer can be discontinuous.

A first layer of titanium dioxide (40) can be present on the first metal film or layer (30) that is on the top surface of the substrate (11) and a second layer of titanium dioxide (41) can be present on the second metal film or layer (31) disposed on the bottom surface (21) of each of the plurality of nanocups (20). The deposition of the first and second titanium dioxide layers, which occurs at the same time, results in a thin coating of titanium dioxide on the sidewalls of the nanocups. The $TiO_2$ coating can be discontinuous.

A third metal film or layer (32) can be present on the first layer of titanium dioxide (40) and a fourth metal film or layer (33) can be present on the second layer of titanium dioxide (41). An adhesion layer of, for example, titanium can be present between the third metal film layer and the first layer of titanium dioxide. Due to the manufacturing process (described in detail below) the fourth metal layer can have a thin layer of titanium dioxide (which can be discontinuous) between the metal layer and the sidewalls of the nanocup. See FIG. 17. The deposition of the third and fourth metal film layers, which occurs at the same time, results in a thin coating of the metal or deposition of metal nanoparticles on the sidewalls of the nanocups. This layer can be discontinuous.

It is expected that some of the adhesion layer material may occur on the sidewall. The adhesion layer material will form in nanoparticles due to the directional deposition. The nanoparticles will be very small because the layer thickness is so much less than the other layers.

The first metal layer can be about 40 to about 120 nm thick (e.g., about 40, 50, 60, 70, 80, 90, 100, 110, 120 nm thick) on the top surface of the substrate. The second metal layer can be about 40 to about 120 nm thick (e.g., about 40, 50, 60, 70, 80, 90, 100, 110, 120 nm thick) on the bottom surface of the nanocup. The third metal layer can be about 40 to about 120 nm thick (e.g., about 40, 50, 60, 70, 80, 90, 100, 110, 120 nm thick) on the surface of the first titanium dioxide layer. The fourth metal layer can be about 40 to about 120 nm thick (e.g., about 40, 50, 60, 70, 80, 90, 100, 110, 120 nm thick) on the surface of the second titanium dioxide layer. The first titanium dioxide layer can be about 40 nm to about 120 nm thick (e.g., about 40, 50, 60, 70, 80, 90, 100, 110, 120 nm thick) on the surface of the first metal layer. The second titanium dioxide layer can be about 40 nm to about 120 nm thick (e.g., about 40, 50, 60, 70, 80, 90, 100, 110, 120 nm thick) on the surface of the second metal layer. In an embodiment the first, second, third, and fourth metal layers are about 80 to about 90 nm thick. In an embodiment the first and second titanium dioxide layers are about 70 to about 80 nm thick.

The thickness of the first and second metal layers can be about the same. The thickness of the third and fourth metal layers can be about the same. The thickness of the first and second metal layers can be different from the third and fourth metal layers.

As the layers of metal and titanium dioxide are deposited onto the substrate, these materials also coat the sidewall of the nanocups. However, due to the glancing angle deposition, the thicknesses of the metal and titanium dioxide on the sidewalls is less than the metal and titanium dioxide layers on the top surface of the substrate and the bottom surfaces of the nanocups. The metal layers and titanium dioxide layers on the sidewalls can be discontinuous (that is, they may not completely cover the sidewalls). During fabrication, the metal and titanium dioxide on the sidewall are deposited at the same time as what is deposited on the flat surfaces. The thickness of the titanium dioxide layer is approximately the thickness of the titanium dioxide layer on the top of the substrate multiplied by the cosine of the taper angle of the nanocup sidewall. Therefore, if the taper angle is about 85%, the thickness of the titanium dioxide layer on the sidewalls will be about 9% of the thickness of the titanium dioxide on the top of the substrate. This layer may be continuous or discontinuous due to the relatively small amount of titanium dioxide deposited on the sidewalls. Therefore, the thickness of the titanium dioxide on the sidewalls can be about 1, 2, 3, 4, 5, 6, 7, 8, 9, 10, 11, 12 nm or more.

Due to the manufacturing process, a very thin layer of metal or a plurality of metal nanoparticles (50) (e.g., gold, silver, a mixture of gold and silver, aluminum, copper, platinum, and mixtures thereof) can be present on the at least one sidewall surface of the plurality of nanocups.

The metal nanoparticles on the sidewalls are formed in a similar manner as to the titanium dioxide deposition through glancing angle deposition. The metal nanoparticles can be single monolayer of metal with an about 20 to about 40 nm diameter (e.g. about 20, 25, 30, 35, 40 nm diameter). In an alternative embodiment, the metal nanoparticles are a single, double or triple layer or combinations thereof of metal. The properties of the metal nanoparticles, the ability for titanium dioxide to coat the sidewalls, and the ability for metal nanoparticles to form will change with the thickness of the second metal layer. The plurality of metal nanoparticles can be arranged in a discontinuous manner.

In an embodiment one or more analytes or specific binding substances are present on the sidewalls of the nanocups, on the bottoms of the nanocups, or on a combination of the sidewalls and the bottoms of the nanocups. The presence of analytes or specific binding substances on the sidewalls can shift the resonances more noticeably than when present on the top of the substrate surface or the bottom or the nanocups because the optical field is very strong on the sidewalls.

Method of Manufacture

In an embodiment an array of polymer nanocups can be fabricated using a nanoreplica molding process. For example, a UV-curable polymer (e.g., NOA-61) can be applied on top of a wafer-scale quartz mold (e.g., a quartz mold) having an array of tapered nanopillars. A backing sheet or layer, such as a polyethylene terephthalate (PET) sheet backing can be placed on top of the UV-curable polymer and the polymer can be evenly spread and then cured in a UV oven. The polymer nanocups can then peeled from the mold.

The metal-titanium dioxide-metal multilayer structure on the polymer nanocup array can be fabricated by, for example, e-beam and sputtering deposition. A metal layer can first deposited by e-beam. A Ti adhesion layer, for example a 5, 6, 7, 8, 9, 10, 11, 12 nm or more adhesion layer can be used. A titanium dioxide layer is then deposited by, e.g., sputtering deposition followed by the second metal layer with, optionally, another Ti adhesion layer (e.g., a 5, 6, 7, 8, 9, 10, 11, 12 nm or more thick adhesion layer). E-beam evaporation can be used to deposit the metallic layers since the directional deposition method can result in metallic nanoparticles on the tapered nanocup sidewalls, which can enhance the LSPR plasmonic effect. Sputtering deposition can be used for the titanium dioxide layers to make the cavity layer as conformal as possible.

Directional deposition can be used for the metal layers (in the examples, by e-beam deposition) and non-directional/conformal deposition for the titanium dioxide layer (in the examples by sputtering). This can lead to the different physical properties of the materials on the nanocup sidewalls.

Specific Binding Substances, Analytes, and Binding Partners

In an embodiment, one or more specific binding substances or analytes are present on the bottom, sidewalls, or both the bottom and sidewalls of the plurality of nanocups. A specific binding substance can bind to binding partner. A binding partner is a substance that forms a complex with a specific binding substance through, for example, ionic bonds, hydrogen bonds, Van der Waals forces, covalent bonds, non-covalent bonds, electrostatic interactions, 7-effects, or hydrophobic effects.

In an example, a specific binding substance is an antibody and a binding partner is a polypeptide that specifically binds to the antibody. In another example, a specific binding substance is a polypeptide and a binding partner is an antibody that specifically binds to the specific binding substance. An analyte can be detected by methods described herein, and can be capable of interacting with molecules added to the nanaocups (such as an enzyme).

A specific binding substance or analyte can be covalently or non-covalently bound to the bottom of the plurality of nanocups. The binding can be due to natural adsorption of molecules on the surface (e.g., due to Van der Waals reaction). In an embodiment, specific binding substances or analytes can be bound to the nanocups via linkers. A specific binding substance can specifically bind to or otherwise interact with one or more binding partners. An analyte, specific binding substance, or binding partner can be, for example, a nucleic acid (DNA, RNA or analogs thereof), polypeptide, protein solution, peptide solution, single- or double-stranded DNA solution, RNA solution, RNA-DNA hybrid solution, solution containing compounds from a combinatorial chemical library, antigen, polyclonal antibody, monoclonal antibody, single chain antibody (scFv), F(ab) fragment, F(ab')2 fragment, Fv fragment, or other specific binding fragment of an antibody, small molecule or metabolite, cell (e.g., a eukaryotic cell, prokaryotic cell, mammalian cell, or any other type of cell), virus, bacteria, polymer, enzyme, peptidomimmetic, ion, aptamer, environmental sample, a food sample, a drug sample, or biological sample. A small molecule or metabolite means a multi-atom molecule other than proteins, peptides and DNA: the term can include but is not limited to amino acids, steroid and other small hormones, metabolic intermediate compounds, drugs, drug metabolites, toxicants and their metabolites, and fragments of larger biomolecules.

A biological sample can be, for example, blood, plasma, serum, gastrointestinal secretions, tissues, tumors, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, prostatic fluid, or any other type of biological sample.

A surface chemistry to immobilize specific binding substances or analytes on the surface of a sensor can be employed. In one embodiment, thiol chemistry can be used to bond thiol modified molecules to the sensor (i.e., an array apparatus containing 1 or more nanocups). In another embodiment, a multilayer assembly based on electrostatic interaction of carboxylate (11-mercaptoundecanoic acid (MUA)) and amino group (poly(ethylenimine)) (MUA-PEI chemistry) can be used. In various other embodiments, methods to functionalize a surface of a sensor include (i) poly (ethylene glycol)-carboxylate (PEG-carboxylate) activated with EDC-NHS and (ii) dextran chemistry.

Devices described herein can be used to detect analytes, specific binding substances, and binding partners in a sample.

Specifically binds means that a specific binding substance binds to binding partner with greater affinity than other non-specific molecules. In the case of antigen/antibody binding a non-specific molecule is an antigen that shares no common epitope with a first antigen that is known to bind to the antibody. In an embodiment a non-specific molecule is not known or recognized to bind to the specific binding substance. For example, an antibody raised against a first antigen to which it binds more efficiently than to a non-specific antigen can be described as specifically binding to the first antigen.

The interaction of specific binding substances and binding partners can be characterized in terms of a binding affinity. For example, a specific binding substance can bind a binding partner with a $K_d$ equal to or less than about $10^{-7}$ M, such as but not limited to, $0.1$-$9.9 \times 10^{-3}$, $10^{-4}$, $10^{-5}$, $10^{-6}$, $10^{-7}$, $10^{-8}$, $10^{-9}$, $10^{-10}$, $10^{-11}$, $10^{-12}$, $10^{-13}$, $10^{-14}$, $10^{-15}$ or any range or value therein. A ligand can bind an analyte with an off rate ($K_{off}$) of less than or equal to $0.1$-$9.9 \times 10^{-3}$ sec$^{-1}$, $10^{-4}$ sec$^{-1}$, $10^{-5}$ sec$^{-1}$, $10^{-6}$ sec$^{-1}$, $10^{-7}$ sec$^{-1}$. A specific binding partner can bind a binding partner with an on rate ($K_m$) greater than or equal to $0.1$-$9.9 \times 10^3$ M$^{-1}$ sec$^{-1}$, $10^4$ M$^{-1}$ sec$^{-1}$, $10^5$ M$^{-1}$ sec$^{-1}$, $10^6$ M$^{-1}$ sec$^{-1}$, $10^7$ M$^{-1}$ sec$^{-1}$, $10^8$ M$^{-1}$ sec$^{-1}$.

One or more specific binding substances or analytes can be attached to a sensor surface (i.e., a nanocup array device) by physical adsorption (i.e., without the use of chemical linkers). In an embodiment one or more specific binding substances or analytes can be attached to a sensor surface by chemical binding (i.e., with the use of chemical linkers). Chemical binding can generate stronger attachment of specific binding substances on a surface and can provide defined orientation and conformation of the surface-bound molecules. Chemical binding can include, for example, amine activation, aldehyde activation, and nickel activation. These surfaces can be used to attach several different types of chemical linkers to a sensor surface. An amine surface can be used to attach several types of linker molecules, while an aldehyde surface can be used to bind proteins directly, without an additional linker. A nickel surface can be used to bind molecules that have an incorporated histidine ("his") tag.

A specific binding substance or analyte can be applied to one nanocup or can be applied across 2, 5, 10, 20, 30 or more nanocups.

Systems

A system can comprise a nanocup apparatus as described herein and a white light source or an LED light source. In an embodiment, a system comprises a nanocup apparatus as described herein, a white light source or an LED light source, a beam collimator, a beam expander, an objective lens and an imaging camera. In an embodiment a system does not comprise a spectrometer. In an embodiment, a system is handheld, compact, and portable. In an embodiment a system is about 5 pounds, 4 pounds, 3 pounds, 2 pounds, 1 pound or less. In an embodiment, the system is about 12 inches by 12 inches by 12 inches; about 6 inches by 6 inches by 6 inches; about 3 inches by 3 inches by 3 inches; about 1 inch by 1 inch by 1 inch or smaller.

In an embodiment, a system comprises a white light or LED light source, and a computing device having a camera; an opaque housing defining a chamber, wherein the housing has a slot or opening that is configured to permit ingress and egress of a nanocup device within the chamber. The light source can be positioned within the chamber or outside of the chamber. If the light source is outside of the chamber, then an opening is provided in the housing for the light source. Regardless of the position of the light source, it is positioned so that the light from the light source can be directed to the nanocup device. The computing device and camera can be positioned within the chamber or outside of the chamber. If the computing device and camera are outside of the chamber, then an opening is provided in the housing for the computing device and camera. Regardless of the position of the computing device and camera, they are positioned so that the light transmitted or reflected from the nanocup device can be detected by the camera. A computing device and/or camera can be user-supplied and can be simple as, for example, a phone.

Methods of Use

An embodiment provides a method of detecting binding of one or more specific binding substances and their respective binding partners using the nanocup device described herein. The methods can comprise applying one or more binding partners to a nanocup device wherein one or more specific binding substances are immobilized on the at least one sidewall, the bottom surface of the nanocups, or both of the at least one sidewall and the bottom surface of the nanocups. The device can be washed to remove unbound binding partners. The nanocup device can be illuminated with a white light source or LED light source. In an embodiment the light has a wavelength of 700 nm (peak) or 623 nm (reference) wavelength. It is noted that the peak and the reference wavelengths can change depending on the geometry of the sensor. If different materials, different thicknesses, or a different nanocup geometry is used then the peak and reference wavelengths can change. One of skill in the art can determine the peak and reference wavelengths for a particular sensor. A relative intensity is detected by a camera. Where the one or more specific binding substances have bound to their respective binding partners, the relative intensity is increased as compared to a situation where one or more specific binding substances have not bound to their respective binding partners. For control or comparison purposes a reading of relative intensity can be completed prior to the application of the one or more binding partners to the device or a previously determined control number can be used.

An embodiment provides a method of detecting one or more analytes on a nanocup device described herein. One or more analytes can be applied or immobilized to the device. The device can be washed. The device can be illuminated with a white light source or a LED light source. In an embodiment the light has a wavelength of 700 nm (peak) or 623 nm (reference) wavelength. A relative intensity is detected by a camera. Where the one or more analytes are present on the at least one sidewall, the bottom surface of the nanocups, or both of the at least one sidewall and the bottom surface of the nanocups the relative intensity is increased as compared to a situation where the one or more analytes are not present on the device. For control or comparison purposes a reading of relative intensity can be completed prior to the addition of the one or more analytes or a previously determined control number can be used.

In an embodiment, one or more analytes can be applied to the nanocup device so that the one or more analytes are present on the at least one sidewall, the bottom surface of the nanocups, or both of the at least one sidewall and the bottom surface of the nanocups. A relative intensity reading can be taken. Then one or more compounds or molecules can be added to the nanocup device. The one or more compounds or molecules can be washed from the nanocup device. A relative intensity reading can be taken. Where the one or more compounds or molecules alter the one or more analytes (e.g., alter the conformation, cleave a portion of the analyte, bind to the analyte, etc.) the relative intensity can change as compared to a situation where the one or more analytes have not been altered by a molecule or compound. A relative intensity can be increased where a compound or molecule has bound to the one or more analytes. A relative intensity can be decreased where, for example, a portion of the one or more analytes are cleaved from the surface of the nanocups. An optional step of detecting a relative intensity can be done prior to the addition of the analytes to the nanocup device.

Advantageously, increases in relative transmission intensity at the peak resonance wavelength with increasing superstrate RI and with no spectral shift can be detected. It is noted that a reflectance measurement instead of a transmission measurement can also be used. Furthermore, there are spectral regions where there is little or no change in transmission intensity. These spectral regions can be used as internal device references. These changes can be detected without a spectrometer. The sensitivity can be greater than 500, 600, 700, or 800 Δ% T/RIU. Additionally, specific binding substance-binding partner binding reactions (e.g., antigen-antibody binding) can be detected at a limit of detection of 100, 50, 20, 10 ng/mL or better.

Manufacture

Methods are provided for making a nanocup array device as described herein. A substrate can be made having a plurality of nanocups. An initial metal layer can be deposited by e-beam evaporation on the substrate having a plurality of nanocups. An adhesion layer for the metal layer, such as titanium, can be used. The adhesion layer can be about 3, 4, 5, 6, 7, 8, 9, 10, 15 nm or more thick. A titanium dioxide layer is then deposited by sputtering deposition onto the substrate. Another metal layer is deposited by e-beam evaporation on the substrate. An adhesion layer for the metal layer, such as titanium, can be used. The adhesion layer can be about 3, 4, 5, 6, 7, 8, 9, 10, 15 nm or more thick. Due to the application process the metal/titanium dioxide/metal layers are deposited on the sidewalls of the nanocups is at a thickness that is less than the thickness of the metal/titanium dioxide/metal layers on the top of the substrate surface and the bottom of the nanocups. The metal/titanium dioxide/metal layers on the sidewalls may be discontinuous. The method can further comprise immobilizing one or more specific binding substances or analytes to the sidewalls of the nanocups, the bottoms of the nanocups, or both the sidewalls and bottoms of the nanocups.

The present disclosure provides an unexpected improvement over U.S. Pat. No. 9,464,985 (Liu et. al.), which is hereby incorporated by reference.

The following are provided for exemplification purposes only and are not intended to limit the scope of the invention described in broad terms above.

EXAMPLES

Example 1. Metal-Insulator-Metal Nanocup Device Fabrication

The processing steps for the complete MIM plasmonic nanocup array sensors begin by fabrication of the polymer nanocups using a nanoreplica molding process. A pipette is used to deposit 2 mL of UV-curable polymer (NOA-61) on top of a wafer-scale quartz mold consisting of an array of tapered nanopillars. A polyethylene terephthalate (PET) sheet backing is placed on top of the UV-curable polymer and once the polymer is evenly spread, it is cured in a UV oven. The polymer nanocups are then peeled from the quartz mold. The Au-titanium dioxide-Au multilayer structure on the polymer nanocup array is fabricated by e-beam and sputtering deposition. The Au layer is first deposited by e-beam with a 9 nm Ti adhesion layer. The titanium dioxide layer is then deposited by sputtering deposition followed by the second Au layer with a 5 nm Ti adhesion layer. E-beam evaporation is used to deposit the metallic layers since the directional deposition method will result in metallic nanoparticles on the tapered nanocup sidewalls, which will enhance the LSPR plasmonic effect. Sputtering deposition is used for the titanium dioxide to make the cavity layer as conformal as possible.

Example 2. Tilted SEM Image of Metal-Insulator-Metal Nanocup Array

A tilted SEM image of the metal-insulator-metal (MIM) nanocup array device consisting of a 90 nm bottom Au layer, 80 nm titanium dioxide insulator layer, and 90 nm top Au layer is shown in FIG. 6. From the tilted image, the Au nanoparticles that form along the cup sidewall are more clearly visualized.

Example 3. Schematic of Simulated Planar Multilayer

Figure 7:
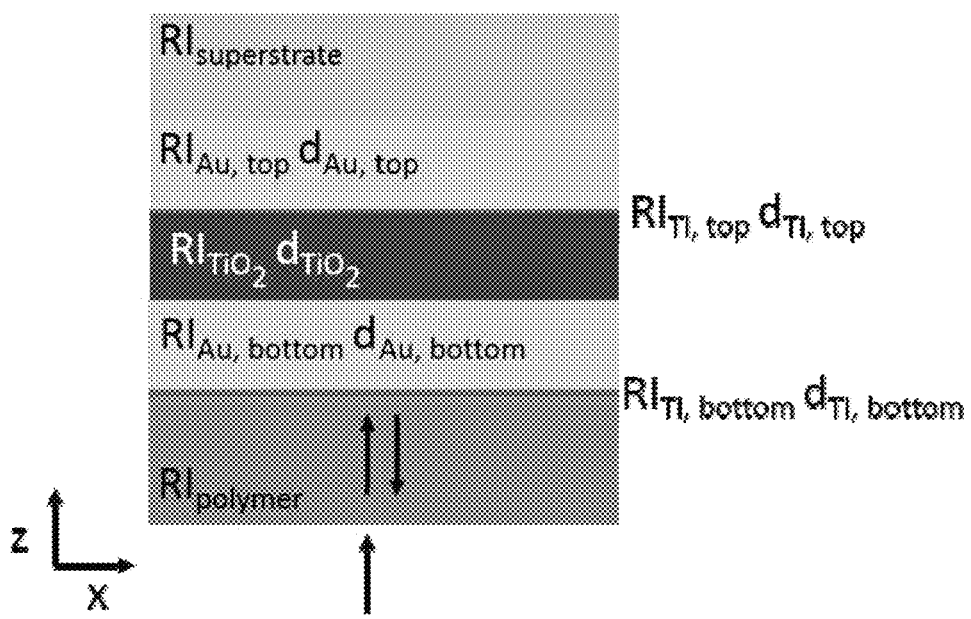
FIG. 7. Schematic of the planar multilayer sensor simulated using the TMM. Each layer is assigned a RI value and a thickness.

A schematic of the planar multilayered structure, simulated using the transfer matrix method (TMM), is shown in FIG. 7. The multilayer consists of 7 layers and therefore 6 interfaces and it is assumed that each layer is flat, homogeneous, and extends infinitely in x and y directions.

Example 4. Transmission Spectra for Different Device Configurations

Figure 8:
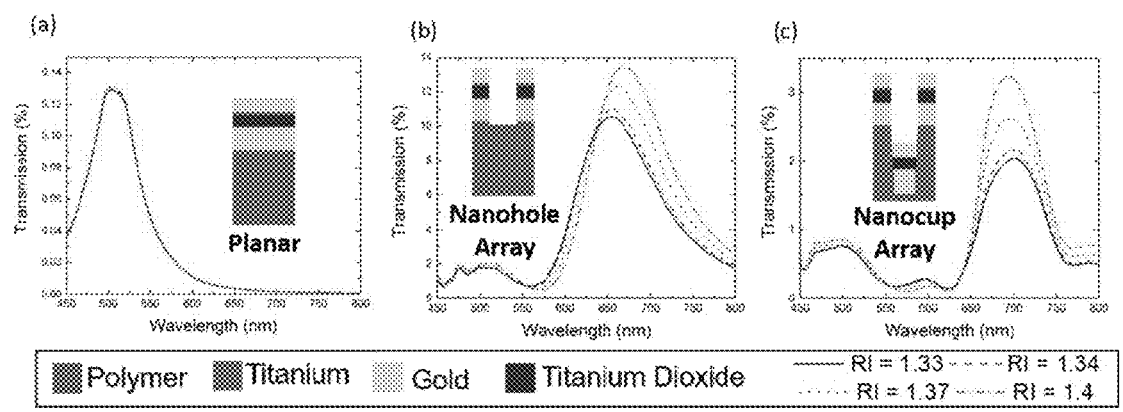
FIG. 8. Spectral features of different device configurations with RI changes. Transmission spectra with increasing superstrate RI values for the (a) planar MIM structure, (b) MIM nanohole array, and (c) MIM nanocup array.

An effective MIM nanocup device design can obtain spectral features where an increase in RI results in an increase in transmission intensity at the peak resonance wavelength with no spectral shift. Therefore, a 3D-FEM study was used to investigate whether these spectral properties can be obtained with different device configurations. The transmission spectra for the planar multilayer structure, MIM nanohole array, and MIM nanocup array with increasing RI values are shown in FIGS. 8a-8c, respectively. In all cases, the bottom Au layer is 90 nm, the titanium dioxide cavity layer is 40 nm, and the top Au layer is 50 nm. As can be seen, the optical effect of a sensitive relative transmission intensity increase with increasing superstrate RI without a spectral shift is only obtained for the MIM nanocup array. The MIM nanohole array shows an increase in transmission intensity, but with a spectral shift. Likely the nanohole array is insufficient to form an adequate MIM cavity structure.

Example 5. Near-Field Electric Field Distribution (z Component)

Figure 9:
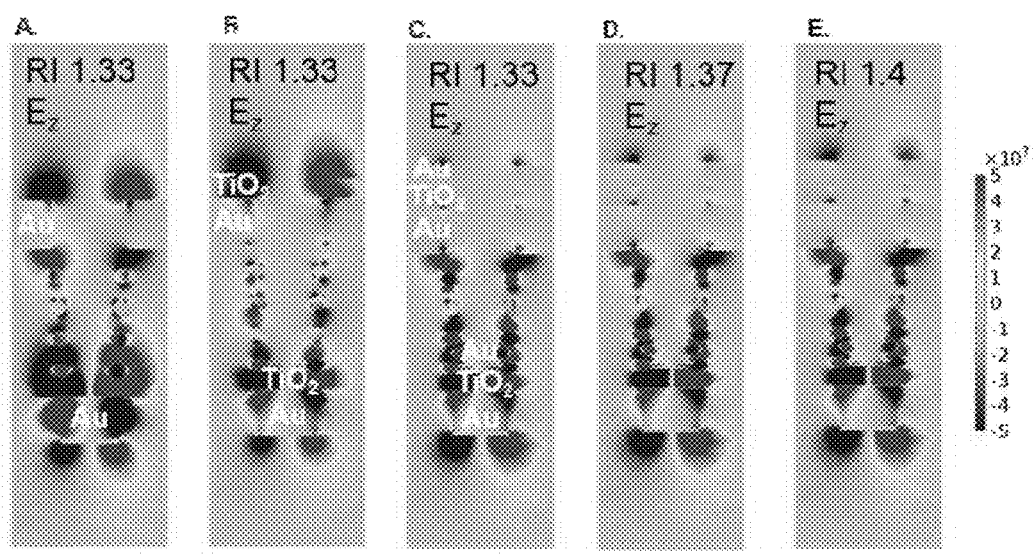
FIG. 9. $E_z$ for different nanocup structures. $E_z$ is shown for the nanocup array with 90 nm bottom Au layer only (A), with bottom Au layer and 40 nm titanium dioxide layer (B) and for the MIM structure with 50 nm top Au layer for RI=1.33 (C), RI=1.34 (D), and RI=1.4 (E).

The z component of the near-field electric field distribution ($E_z$) is shown in FIG. 9 for the nanocup with different layers to visualize the field penetration into the metal and dielectric materials. FIG. 9A shows $E_z$ for the nanocup with a 90 nm gold (Au) layer only. The nanocup with a bottom Au layer and 40 nm titanium dioxide (titanium dioxide) cavity layer is shown in FIG. 9B. The $E_z$ distribution for the MIM nanocup with a 50 nm top Au layer is shown for RI values of 1.33 (FIG. 9C), 1.37 (FIG. 9D), and 1.4 (FIG. 9E). For the nanocup device with the bottom Au layer only or bottom Au layer with titanium dioxide layer, the z component of the electric field is clearly confined at the metal-dielectric interfaces. In both cases, the fields extend similarly into the superstrate dielectric. However, for the device with the cavity layer, there is some additional field confinement at the bottom of the nanocup. In the case of the MIM nanocup structure, there is additional field confinement at the bottom and top of the nanocup such that there is relatively little extension of the field into the dielectric superstrate. However, as the RI increases, there is a clear enhancement in the amount of field interacting with the superstrate dielectric at the top of the nanocup.

Example 6. Resonance Tuning in Planar MIM Sensor

Resonance tuning the planar MIM sensor was carried out using the TMM to compare the results to those obtained using the 3D-FEM simulation of the MIM nanocup array. The transmission spectra for a MIM structure with a 90 nm bottom Au layer and 90 nm top Au layer are shown in FIG. 10A with cavity layers from 40 nm to 120 nm with a 10 nm step size. For the smaller cavity thicknesses (40-60 nm), there is only a single peak around 500 nm. However, as the cavity layer increases, a second peak occurs at longer wavelengths. The peak at 500 nm is due to well-known optical properties of Au thin films and can be considered as a photoluminescence (PL) peak. The second peak at longer wavelengths is the cavity mode of interest. FIG. 15B shows the transmission intensity at this cavity peak as a function of cavity thickness and FIG. 10C shows the ratio of the transmission intensity for the cavity peak to the PL peak. The data in FIG. 10B-10C are for top Au thicknesses of 50 nm, 75 nm, and 90 nm with a fixed bottom Au thickness of 90 nm. The sensitivity, going from a RI value of 1.33 to 1.34, is shown in FIG. 10D.

Example 7. Varying Top and Bottom Au Layers

Figure 11:
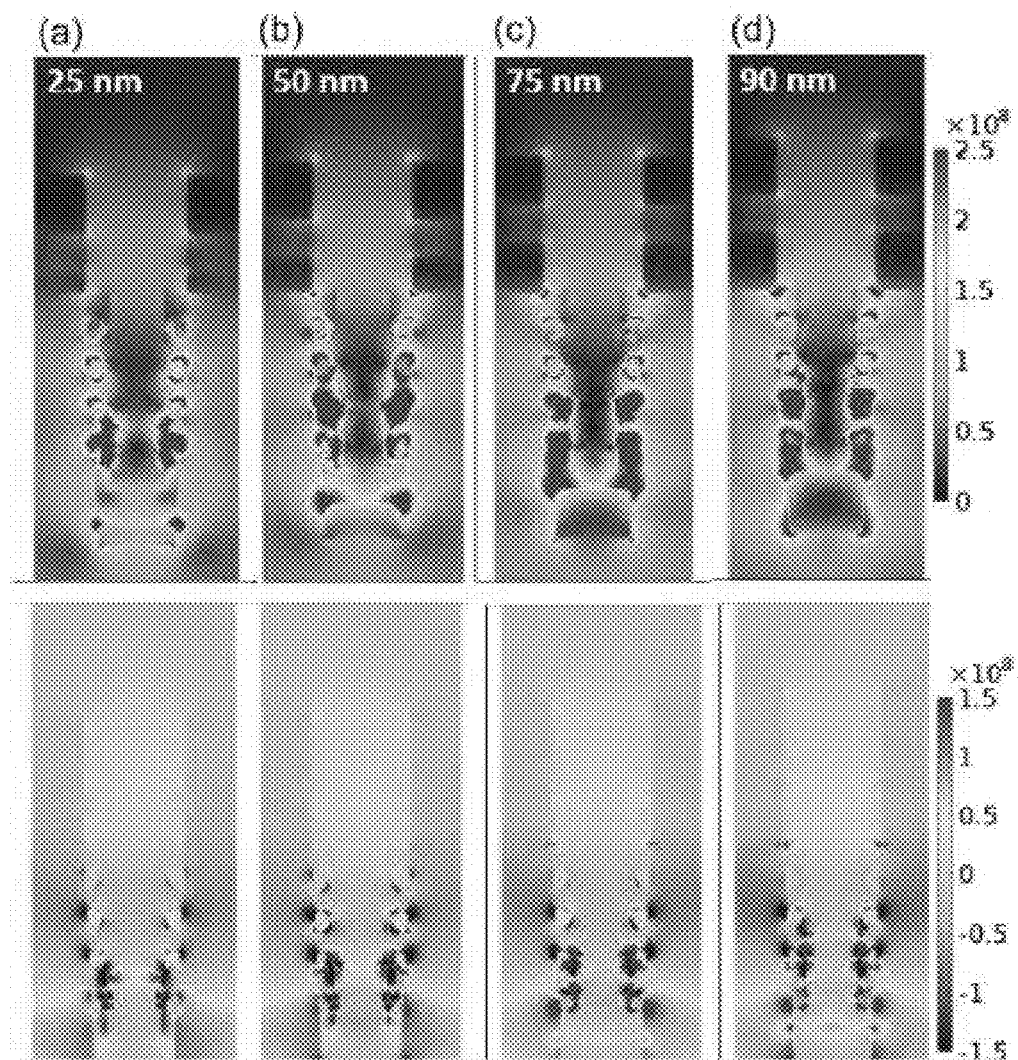
FIG. 11. Field confinement and spectral effects of varying top Au thickness. |E| and $E_x$ are shown for RI=1.33 for a nanocup with a bottom Au layer of 90 nm, titanium dioxide cavity layer of 60 nm, and top Au layer of 25 nm (a), 50 nm (b), 75 nm (c), and 90 nm (d). Transmission spectra with increasing RI values (1.33, 1.34, 1.37, and 1.4) for top Au layers of 25 nm (e), 50 nm (f), 75 nm (g), and 90 nm (h).
Figure 11:
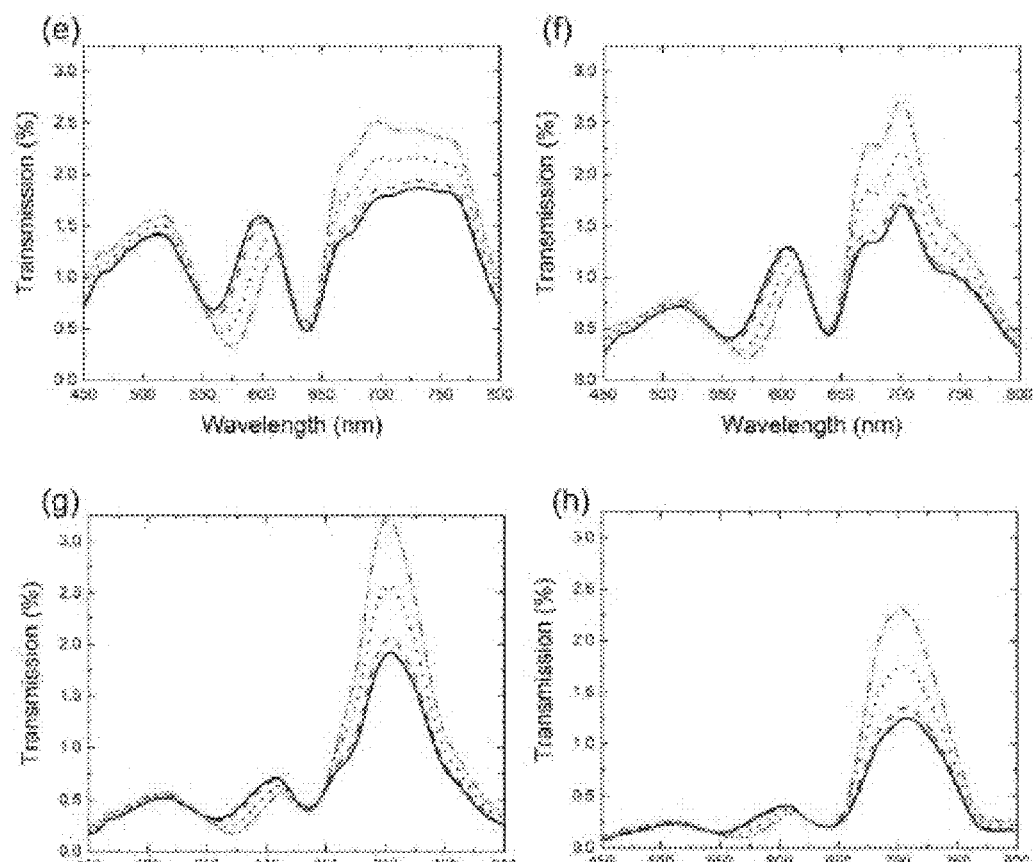
Figure 12:
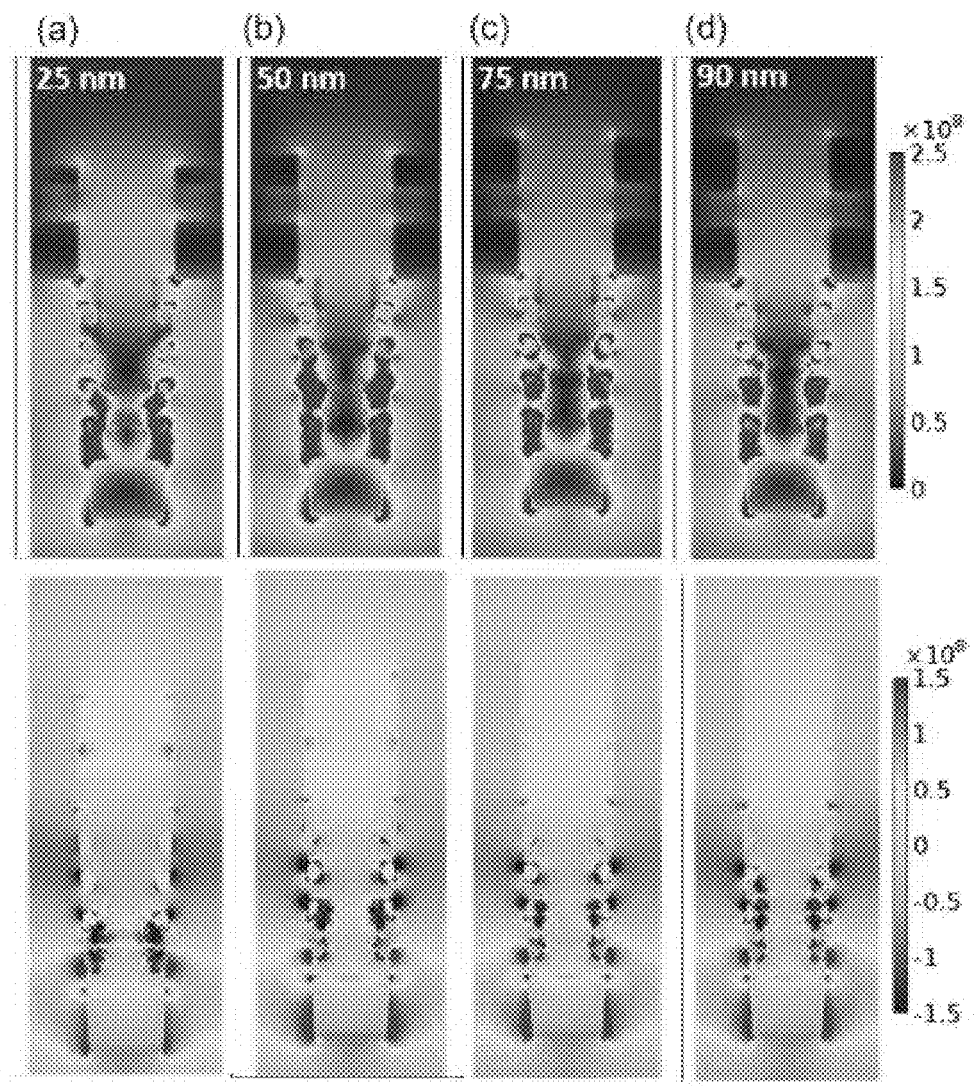
FIG. 12. Field confinement and spectral effects of varying bottom Au thickness. |E| and $E_x$ are shown for RI=1.33 for a nanocup with a titanium dioxide cavity layer of 60 nm, top Au layer of 90 nm, and bottom Au layer of 25 nm (a), 50 nm (b), 75 nm (c), and 90 nm (d). Transmission spectra with increasing RI values (1.33, 1.34, 1.37, and 1.4) for bottom Au layers of 25 nm (e), 50 nm (f), 75 nm (g), and 90 nm (h).
Figure 12:
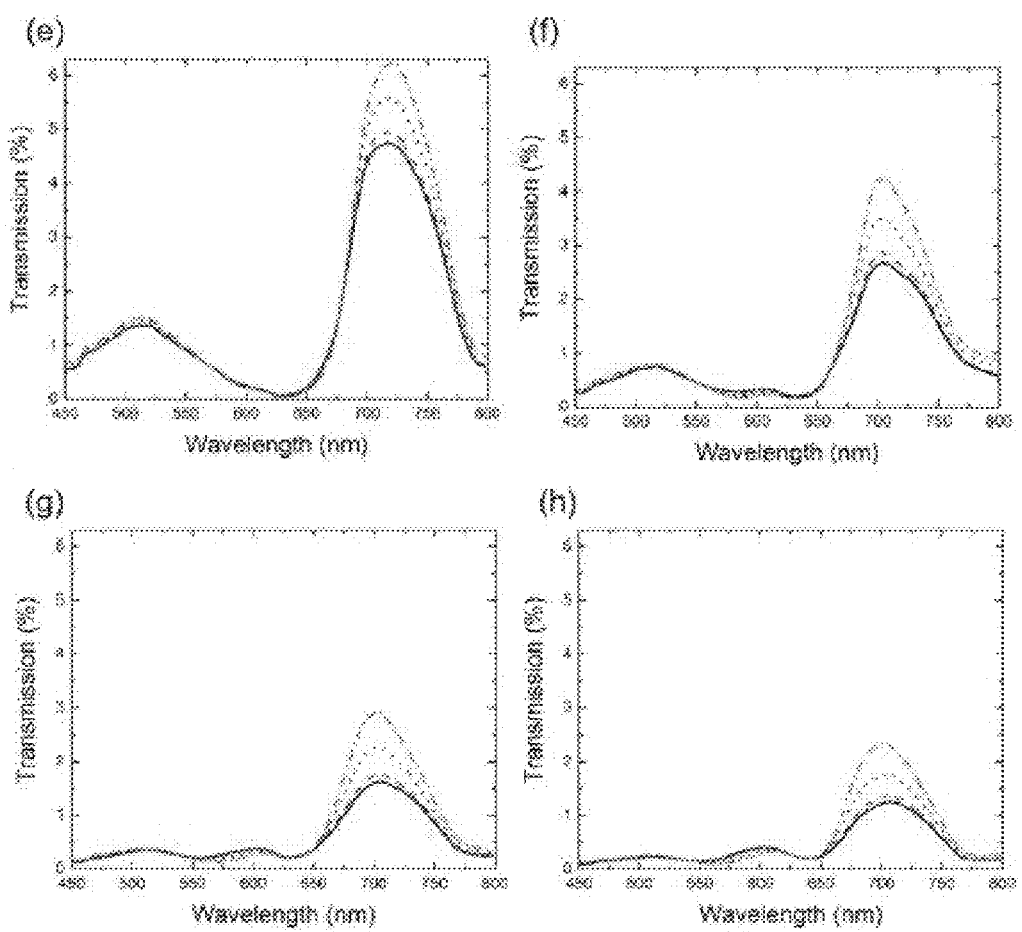

The field localization and spectral effects of changing the top and bottom Au thicknesses are shown in FIG. 11-12. In FIG. 11, the bottom Au layer is fixed at 90 nm, the titanium dioxide cavity layer is fixed at 60 nm, and the top Au layer is varied. |E| and $E_x$ are shown for top Au layers of 25 nm (FIG. 11A), 50 nm (FIG. 11B), 75 nm (FIG. 11C), and 90 nm (FIG. 11D). An increase in the top Au layer leads to increased field localization in the bottom of the nanocup (and less field localization in the top of the nanocup). However, a cavity mode is clearly visualized with the given scaling for all cases. The spectral features with increasing RI values (1.33, 1.34, 1.37, and 1.4) are shown for a top Au show an increase in transmission intensity at the resonance wavelength with increasing RI and no spectral shift.

The same study was repeated, but in this case the bottom Au thickness was varied and the top Au thickness was fixed at 90 nm with a 60 nm titanium dioxide cavity layer. |E| and $E_x$ are shown for bottom Au layers of 25 nm (FIG. 12A), 50 nm (FIG. 12B), 75 nm (FIG. 12C), and 90 nm (FIG. 12D). Increasing the bottom Au layer shows an increase in field localization in the top and bottom of the nanocup. With the current scaling, a cavity mode is only clearly visualized for the 75 nm and 90 nm cases. The spectral features with increasing RI values (1.33, 1.34, 1.37, and 1.4) are shown for a bottom Au layer of 25 nm (FIG. 12E), 50 nm (FIG. 12F), 75 nm (FIG. 12G), and 90 nm (FIG. 12H). Similarly to varying the top Au layer thickness, there is a consistent increase in the transmission intensity at the peak resonance wavelength for all cases. However, there is a significant change in the spectral features, such as the number of prominent peaks, which could potentially impact the sensing performance.

Example 8. Comparing Cavity and Plasmonic Materials

A Fabry-Perot cavity should have low loss and high reflectivity R given by $R=((RI_m-RI_d))\ ((RI_m+RI_d)^2+k^2)$ where $RI_m$ is the RI of the reflector, $RI_d$ is the RI of the dielectric, and k is the extinction coefficient of the reflector. An optimal metal will have a small k and a real part of its RI that is quite dissimilar to that of the cavity layer for high R. Au, silver (Ag), and copper (Cu) have the second property whereas titanium (Ti) does not. Consequently, the R of the titanium dioxide to Au, Ag, and Cu interface is 96%, 99%, and 94%, respectively whereas it is only 54% for Ti. The values of k for the four metals are comparable. The transmission loss going through 90 nm of material will result in transmission values of 0.14%, 0.043%, 0.12%, and 0.17% for Ag, Au, Cu, and Ti, respectively.

An optimal plasmonic material should have a large number of free electrons and low material loss. The Drude model is commonly used to examine the properties of metals for plasmonic applications, where the electrons in the metal are modelled as if they are in a free electron gas. According to the Drude model, the complex dielectric function ($\epsilon'(\omega)+i\ \epsilon''(\omega)$ where $\omega$ is the frequency of the incident light, $\epsilon'(\omega)$ is the real part of the dielectric function, and $\epsilon''(\omega)$ is the imaginary part of the dielectric function for a metal is given by $\epsilon'(\omega)+i\ \epsilon''(\omega)=\epsilon_{int}-(\omega_p^2/\omega(\omega+i\Gamma))$ where $\epsilon_{int}$ is the contribution to the dielectric constant from interband transitions, $\omega_p$ is the plasma frequency, and r is the damping term.[2] Both $\omega_p$ and r are used to classify the metal's properties as a suitable plasmonic material. The number of free electrons is quantified primarily by $\omega_p=Ne^2/\epsilon_0 m^*$ where N is the number of free electrons, e is the charge of the single electron, $\epsilon_0$ is the vacuum permittivity, and m* is the reduced mass of the electron. The material loss is quantified primarily by $\Gamma=1/\tau$ where $\tau$ is the mean electron relaxation time. A summary of the important material parameters for silver (Ag), Au, Copper (Cu), and Ti is shown in Table 1 at $\lambda=700$ nm. Overall, the calculations show that the performances of the plasmonic and MIM devices will be optimized for Ag metallic layers.

TABLE 1

Comparison of different metal parameters for MIM and plasmonic sensing

| Material | R | $\omega_p$ (cm$^{-1}$) | $\Gamma$ (cm$^{-1}$) |
|---|---|---|---|
| Ag | 0.99 | 7.27 × 10$^{-4}$ | 1.45 × 10$^{-2}$ |
| Au | 0.96 | 7.28 × 10$^{-4}$ | 2.15 × 10$^{-2}$ |
| Cu | 0.94 | 5.96 × 10$^{-4}$ | 0.732 × 10$^{-2}$ |
| Ti | 0.54 | 2.03 × 10$^{-4}$ | 3.82 × 10$^{-2}$ |

Figure 13:
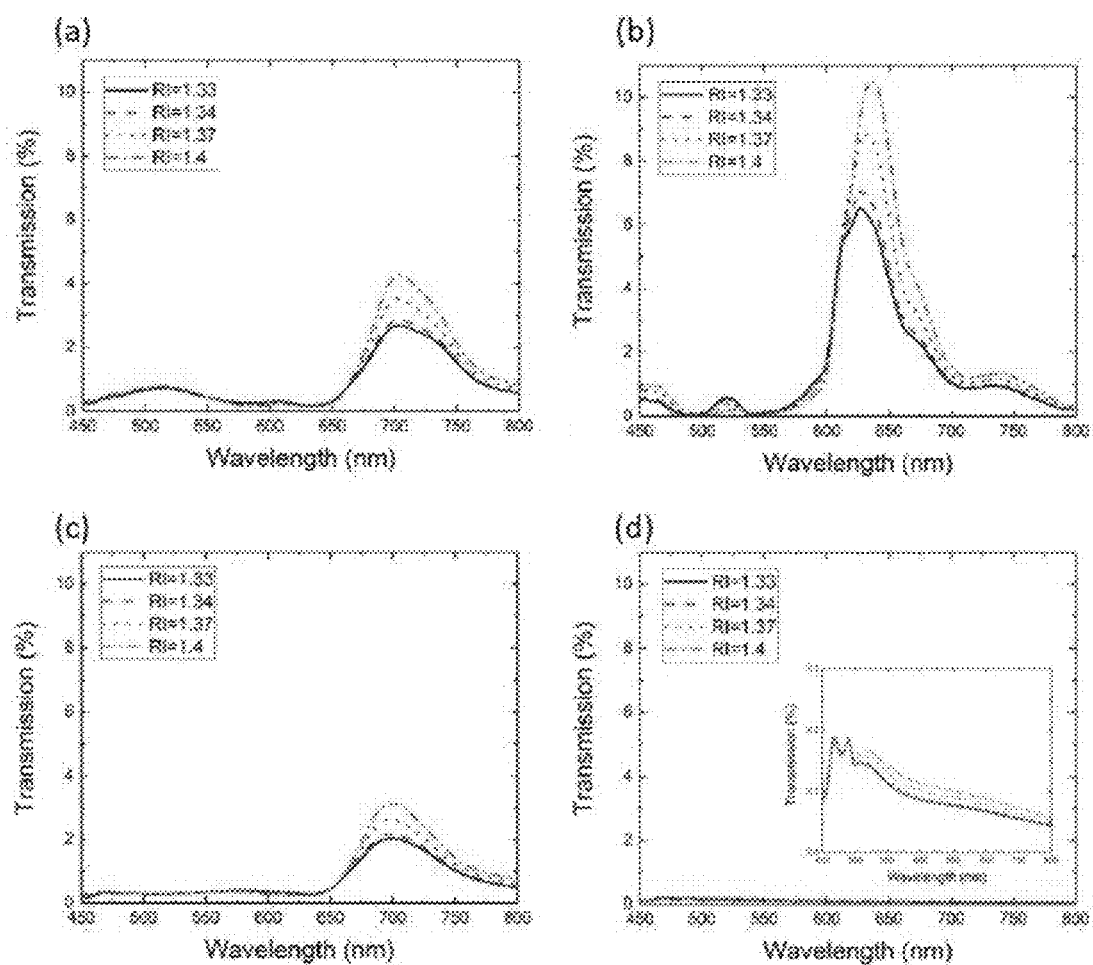
FIG. 13. Comparison of MIM nanocup sensors with different metal materials. Transmission spectra with increasing RI values for MIM nanocups with Au layers (a), Ag layers (b), Cu layers (c), and Ti layers (d). Comparison of MIM nanocup sensors with different metal materials. (e) Normalized electric field distribution |E| for Ag (left) and Ti (right). (f) $E_x$ near-field distribution for Ag (left) and Ti (right).
Figure 13:
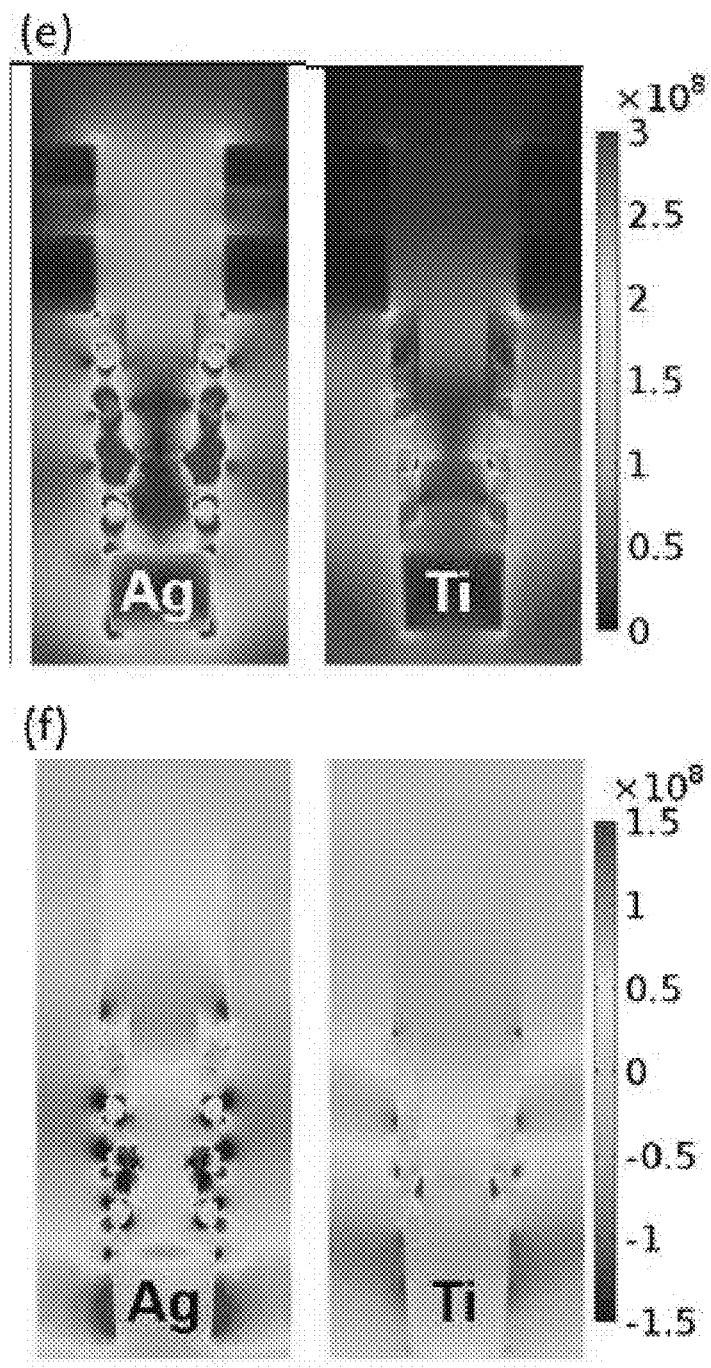

FEM and TMM simulation studies were also carried out on the full device and planar sensor, respectively, to further examine the impact of changing the metal material. FIG. 13 shows the transmission spectra from the 3D-FEM study with the metal material changed to Au (FIG. 13a), Ag (FIG. 13b), Cu (FIG. 13c), and Ti (FIG. 13d), respectively. In all cases, the bottom metal layer is 90 nm, the insulator layer is a 60 nm thick titanium dioxide layer, and the top metal layer is 50 nm. The RI values simulated were 1.33, 1.34, 1.37, and 1.4. For the Au device, the peak wavelength occurs at 700 nm with a transmission intensity of 3% while for the Ag device, the peak wavelength occurs at 625 nm with a transmission intensity of 6%. For the Cu device, the peak wavelength occurs at 700 nm with a transmission intensity of 2% and for Ti the peak wavelength occurs at 525 nm with a transmission intensity of 0.15%. The sensitivity values of the Au, Ag, Cu, and Ti devices are 690 Δ % T/RIU, 890 Δ % T/RIU, 650 Δ % T/RIU, and 250 Δ % T/RIU, respectively. Therefore, when the metal layers are changed from Au to Ag the transmission intensity doubles and the sensitivity improves by 200 Δ % T/RIU.

FIGS. 13e-13f shows the normalized near-field electric field distributions |E| and $E_x$, respectively, for the MIM nanocup device with Ag and Ti metal layers. Each field distribution is shown at the respective resonance wavelengths for the different devices at a RI value of 1.33. As can be seen, on-resonance the Ag device shows localized electric fields at the nanocup top, nanocup bottom, and at the nanoparticles along the cup sidewalls associated with a strong plasmonic component. In addition, a cavity mode with high electric field intensity is strongly confined in the titanium dioxide insulator layer at the bottom of the nanocup. However, for the Ti device, the near-field electric field is weakly localized and no cavity mode can be visualized in the near-field distributions with the given scaling. This is expected since Ti is both a poor plasmonic material and has a low R compared to the other materials, which will result in a poor Q-factor for the cavity. This dependence of the plasmon resonance generation and cavity confinement on the metallic optical properties can explain why the overall transmission of the Ti device is an order of magnitude less than for the Ag device and why the sensitivity for the Ag device is greater than for the Ti device by 640 Δ% T/RIU.

Figure 14:
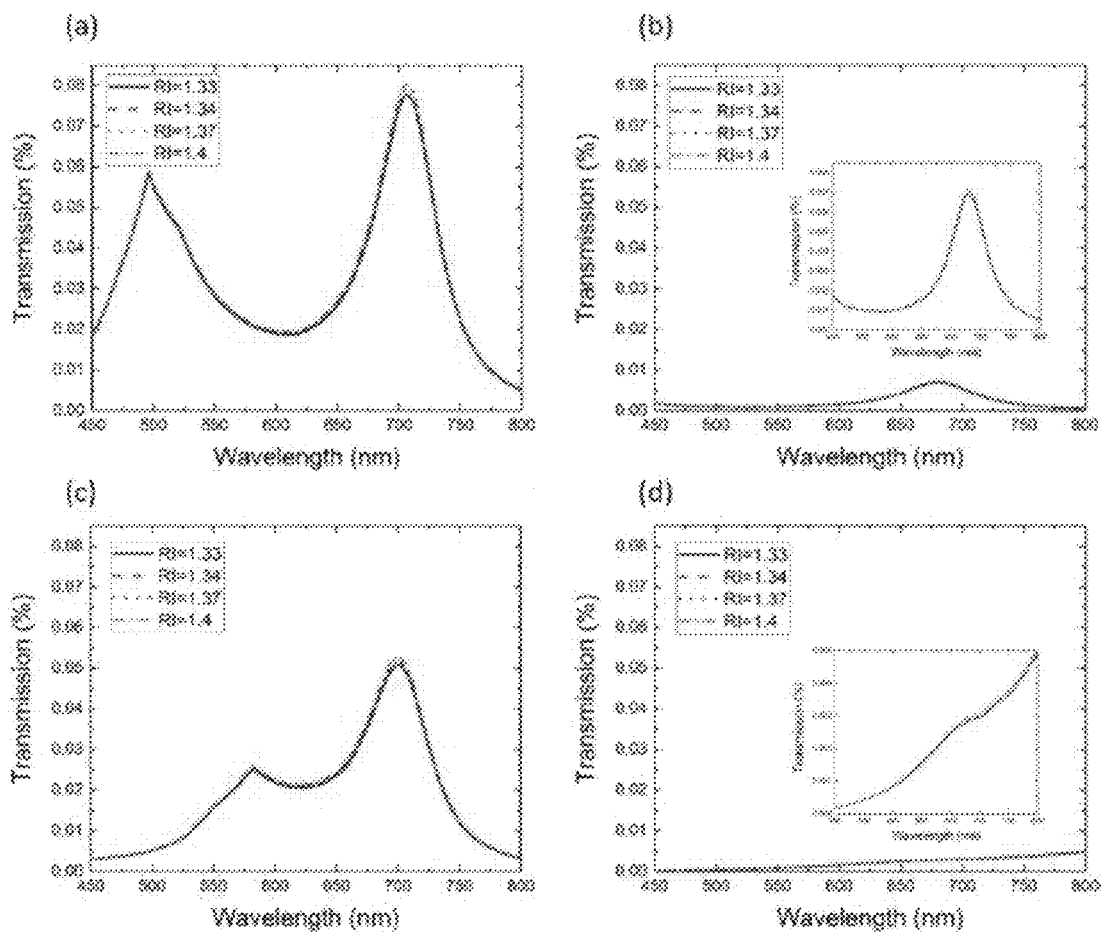
FIG. 14. Comparison of planar MIM sensors with different materials for the metal layers. Transmission spectra with increasing RI values for Au layers (a), Ag layers (b), Cu layers (c), and Ti layers (d).

The transmission spectra for the planar MIM sensor without the plasmonic component, simulated by the TMM, are shown in FIG. 14 for Au (FIG. 14a), Ag (FIG. 14b), Cu (FIG. 14c), and Ti (FIG. 14d). In all cases, the bottom metal layer was 90 nm, the titanium dioxide cavity layer was 100 nm, and the top metal layer was 50 nm. A cavity mode is evident for the Au, Ag, and Cu MIM sensors, but not for the Ti MIM device. On resonance, the transmission intensity for the Au device is 0.08% and the sensitivity is 56 Δ% T/RIU. The transmission intensity for the Ag device is 0.007% with a sensitivity of 59 Δ% T/RIU while the transmission intensity for the Cu device is 0.05% with a sensitivity of 57 Δ% T/RIU. Therefore, the Au device shows the highest transmission intensity, but the lowest performance while the Ag device shows the lowest transmission intensity and the highest sensitivity. However, the sensitivity increase from Au to Ag is only 3 Δ% T/RIU and therefore is relatively insignificant.

Overall, the results show that the device performance in terms of overall transmission and sensitivity can be improved by optimizing the plasmonic materials. However, for practical biosensing applications Au is almost always chosen over Ag because Au is chemically inert and has greatly improved device stability. A combination of Au and Ag can be a good choice for this sensor, such as using Ag for the bottom metal layer and Au for the top metal layer, where there is a trade-off between device performance and stability.

Example 9. Loss in the Insulator Cavity Layer

Figure 15:
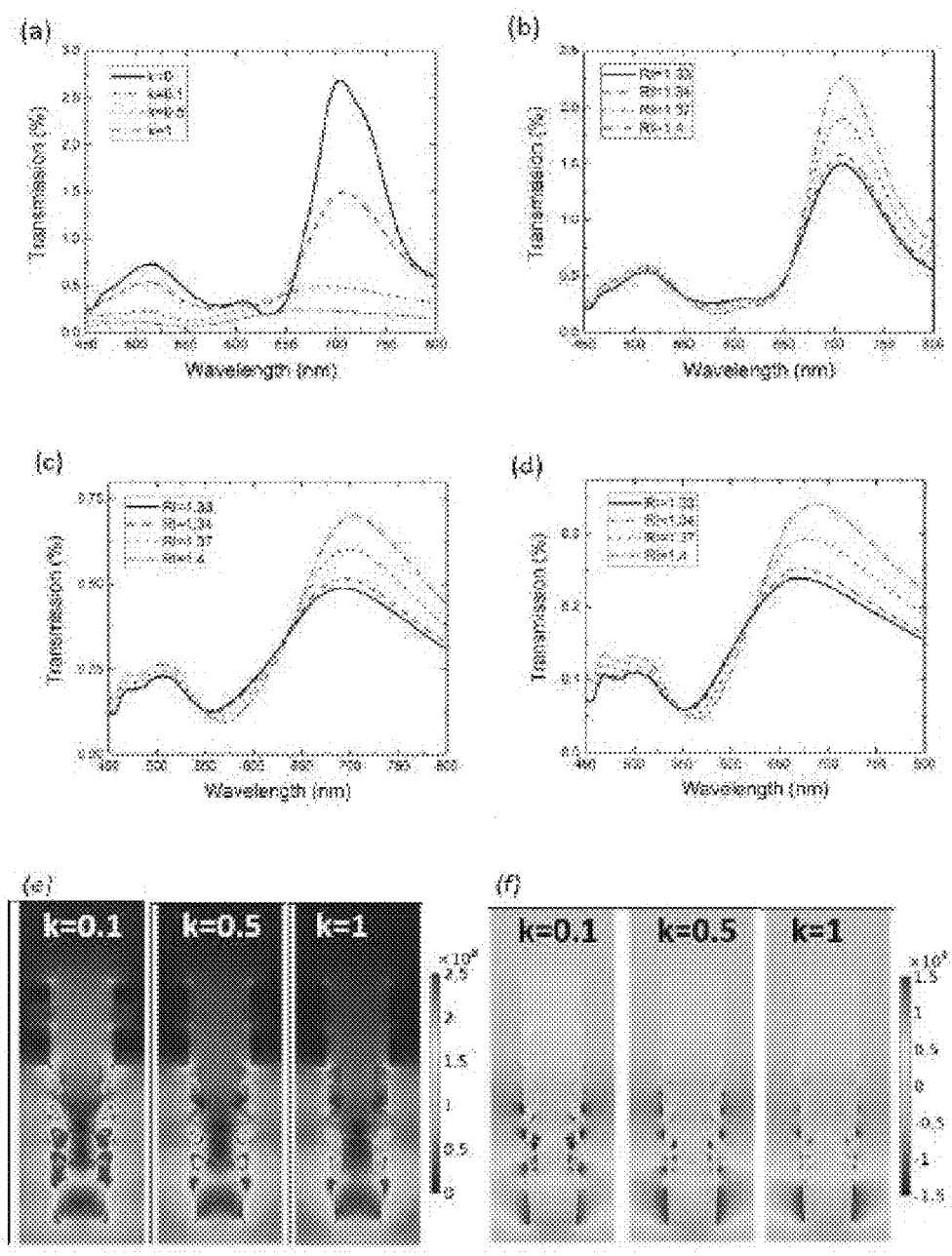
FIG. 15 Analysis of added cavity layer loss for MIM nanocup and planar MIM sensors. (a) Transmission spectra at RI=1.33 for Au MIM nanocup array with increasing k values. Transmission spectra for the MIM nanocup array with increasing RI values for k=0.1 (b), k=0.5. Analysis of added cavity layer loss for MIM nanocup and planar MIM sensors. Transmission spectra for the MIM nanocup array with increasing RI values for k=0.5 (c), and k=1 (d). Normalized electric field distribution |E| for increasing k values (e). (f) A cross-section of a single nanocup showing $E_x$ with increasing k values. Transmission spectra at RI=1.33 for Au planar MIM sensor with increasing k values (g). (h) Transmission spectra with increasing RI values for the planar MIM sensor where k=0.1
Figure 15:
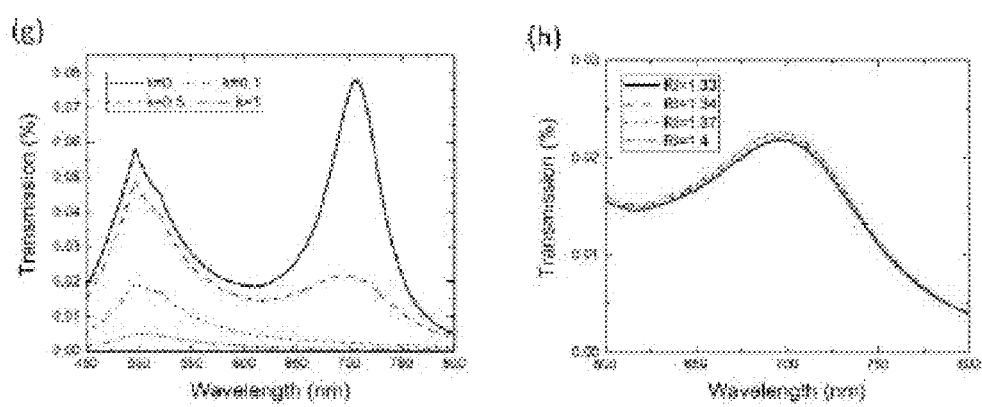
Figure 16:
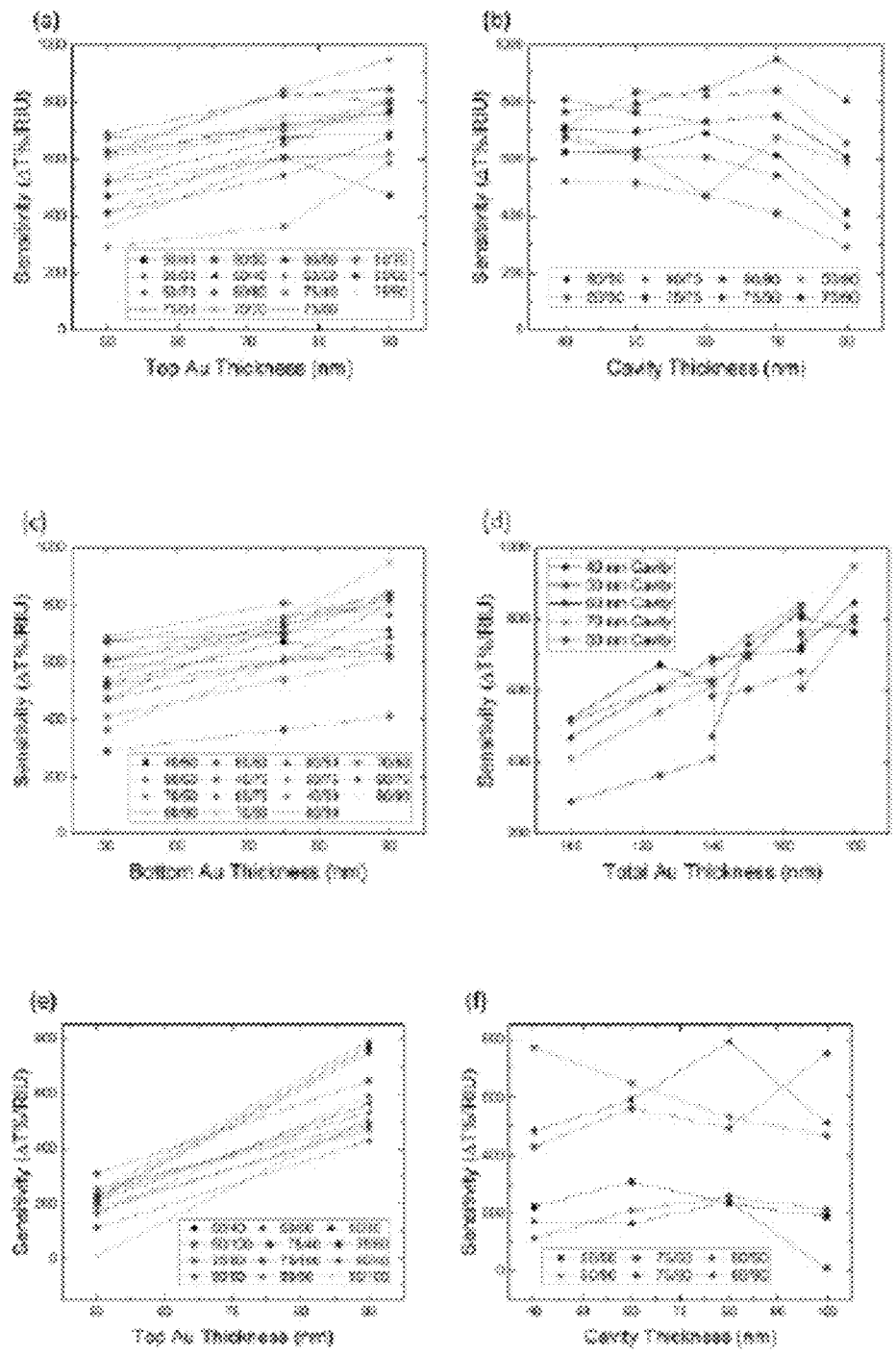
FIG. 16. Comparison of simulation and experiment for sensitivity optimization in MIM nanocup arrays. The simulated sensitivity values are shown as a function of top Au thickness (a), cavity thickness (b). Comparison of simulation and experiment for sensitivity optimization in MIM nanocup arrays. The simulated sensitivity values are shown as a function of bottom Au thickness (c), and total Au thickness (d). For comparison, the experimental sensitivity values are shown as a function of top Au thickness (e) and cavity thickness (f). For comparison, the experimental sensitivity values are shown as a function of bottom Au thickness (g), and total Au thickness (h).
Figure 16:
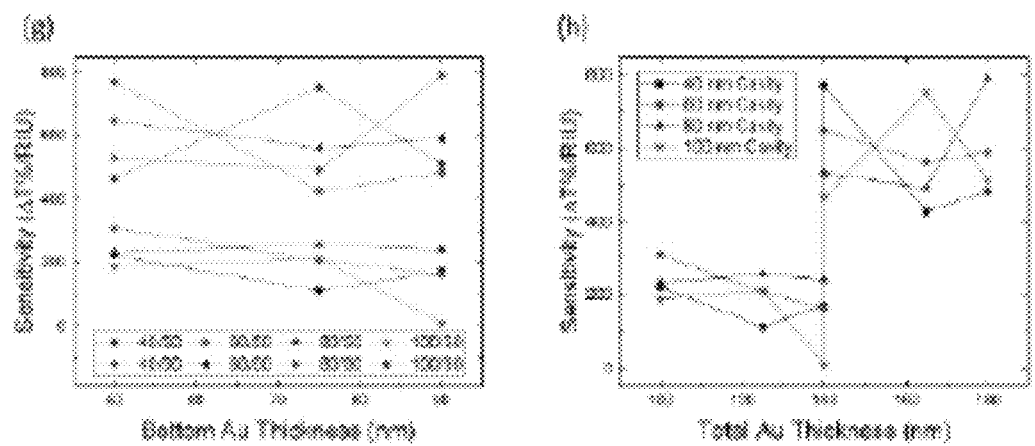

The dependence of the full device and planar sensor performance on loss in the titanium dioxide cavity layer was also studied by simulation with results shown in FIG. 15. In all previous simulations, it was assumed that the extinction coefficient (k) for the titanium dioxide layer is zero. However, if for future applications we wanted to use a semiconductor material instead of an insulating material, it will not be necessarily true that k=0 in our wavelength range of interest. Therefore, it is important to consider the performance of the device as a function of loss in the cavity layer.

FIG. 15a shows the transmission spectra for the full MIM plasmonic nanocup array device for a superstrate RI of 1.33 and k=0, 0.1, 0.5, and 1. With an increase in k, there is a decrease in the transmission intensity, as expected. The transmission spectra with increasing superstrate RI are shown in FIG. 15b-15d for k=0.1, k=0.5, and k=1, respectively. In all cases, the bottom Au layer is 90 nm, the titanium dioxide cavity layer is 60 nm, and the top Au layer is 50 nm. The transmission intensity at the peak for k=0.1 is 1.5% and the sensitivity is 624 Δ% T/RIU. For k=0.5, the transmission intensity on resonance is 0.5% and the sensitivity is 545 Δ % T/RIU, while for k=1 the transmission intensity is 0.25% and the sensitivity is 537 Δ% T/RIU. Therefore, with increasing k there is a decrease in both the transmission intensity and the sensitivity. However, the sensing mechanism is still maintained although in FIG. 15d when k=1 there is a spectral shift in the peak because the high loss results in poor field confinement in the cavity and thus the cavity effects are negligible compared to the plasmonic effects. The near-field electric field distributions on resonance are shown in FIG. 15e (|E|) and FIG. 15f ($E_x$) for different k values as indicated with a superstrate RI of 1.33. As the k value increases, there is a loss in the localized electric fields associated with the excitation of LSPR and the cavity mode becomes less confined.

The transmission spectra for the planar MIM sensor with increasing k values are shown in FIG. 15f. Similarly, with an increase in k, there is a decrease in transmission intensity. However, in contrast to the full device, for k=0.5 and k=1 a resonance can no longer be sustained in the sensor. In all cases, the bottom Au layer is 90 nm, the titanium dioxide cavity layer is 100 nm, and the top Au layer is 50 nm. At k=0 the transmission intensity on resonance is 0.08% and the sensitivity is 56 Δ% T/RIU while at k=0.1 the transmission intensity on resonance is 0.02% and the sensitivity is 24 Δ% T/RIU. With increasing k there is a decrease in the transmission intensity and a significant decrease in the sensitivity. In the full device, the plasmonic component results in an overall increase in transmission intensity and is used to tune the cavity loss and therefore the output power.

Example 10. Cavity Parameter Tuning for Optimized Sensitivity

To assess the feasibility of using Au-titanium dioxide-Au MIM plasmonic nanocavity devices for refractometric sensing, the sensitivity values were determined by simulation and experiment for various devices to identify the parameters that have the largest effect on the sensitivity and to address the performance of these devices. In total, devices with five different cavity thicknesses (40 nm, 50 nm, 60 nm, 70 nm, 80 nm) and three different top and bottom Au layers (50 nm, 75 nm, 90 nm) were simulated. Devices with four different cavity thicknesses (40 nm, 60 nm, 80 nm, 100 nm), two different top Au thicknesses (50 nm, 90 nm), and three different bottom Au thicknesses (50 nm, 75 nm, 90 nm) were fabricated and tested experimentally.

The simulation results of the sensitivity assessments are shown in FIG. 16a-16d and the experimental results are shown in FIG. 16e-16h. In total, devices with five different cavity thicknesses (40 nm, 50 nm, 60 nm, 70 nm, 80 nm) and three different top and bottom Au layers (50 nm, 75 nm, 90 nm) were simulated. Devices with four different cavity thicknesses (40 nm, 60 nm, 80 nm, 100 nm), two different top Au thicknesses (50 nm, 90 nm), and three different bottom Au thicknesses (50 nm, 75 nm, 90 nm) were fabricated and tested experimentally. FIGS. 16a-16d show the simulation results for the sensitivity as a function of the top Au thickness, cavity thickness, bottom Au thickness, and total Au thickness (adding together the bottom and top Au thicknesses), respectively. FIGS. 16e-16h show the experimental results for the sensitivity as a function of the top Au thickness, cavity thickness, bottom Au thickness and total Au thickness, respectively.

Both the simulation and experimental results show that a larger top Au thickness will lead to a higher sensitivity (FIGS. 16a and 16e). FIGS. 16b and 16f show the simulation and experimental results for the sensitivity as a function of the cavity thickness for various different Au layer combinations. However, while the simulation results show that the larger bottom Au thickness will also give a higher sensitivity (FIG. 16c); the experiment (FIG. 16g) does not show the same trend. This difference could be due to several factors in the modelled device geometry. For example, in the model the Au nanoparticles on the sidewalls were fixed at a single layer with diameters of 30 nm. The properties of the Au sidewall nanoparticles, the ability for titanium dioxide to coat the sidewalls, and the ability for Au nanoparticles to form on the top Au layer will change with the bottom Au thickness, but were not taken into consideration in the simulation. Both simulation and experiment show that a sufficient total Au thickness is required to have a high sensitivity (FIG. 16d and FIG. 16h), meaning that high field confinement is crucial for refractometric sensing with this device design.

Example 11. Sensitivity of Device

The transmission spectra with increasing RI values are shown in FIG. 1d. An increase in RI leads to an increase in transmission intensity at a peak resonance wavelength of 700 nm. Here the sensitivity is defined as the relative percent transmission intensity change per refractive index unit ($\Delta$T %/RIU). For this optimized device design, the experimental sensitivity value is 800 $\Delta$T %/RIU. There is no spectral shift at the primary transmission resonance and there are also spectral locations with no transmission intensity change with increasing RI, which can be used as built-in reference points. Transmission measurements are prone to large fluctuations based on factors such as sample defects and contamination and therefore internal device references can help to correct for these instabilities. This device is then suitable for spectrometer-free measurements since it only requires transmission values to be recorded on-resonance and at a reference location.

A finite element method (FEM) model was used to study the sensing mechanism, plasmon-cavity coupling, and cavity confinement in this multilayered nanocup structure. Cross-sectional, top-down, and 3D rotated views of the 3D-FEM model of the MIM plasmonic nanocup device are shown in FIGS. 2a-2c. The simulation consists of a single tapered polymer nanocup modelled in the center of the simulation region with periodic boundary conditions along x and y to simulate the array effect. The transfer matrix method (TMM) was also used to simulate a planar multilayer sensor with no plasmonic component, shown in FIG. 7. A FEM study was first used to investigate whether the spectral properties of the MIM nanocup array can be obtained with different device configurations. The transmission spectra with increasing RI values were simulated for a planar multilayer sensor, a MIM nanohole array, and the MIM nanocup array studied in this work with the results shown in FIG. 8. The optical effect of a sensitive relative transmission intensity increase with increasing superstrate RI without a spectral shift is only obtained for the MIM nanocup array. The MIM nanohole array shows an increase in transmission intensity, but with a reduced sensitivity and a spectral shift. Likely the nanohole array is insufficient to form an adequate MIM cavity structure.

Example 12. Near-Field Electric Field Distributions in the MIM Nanocup

Figure 2:
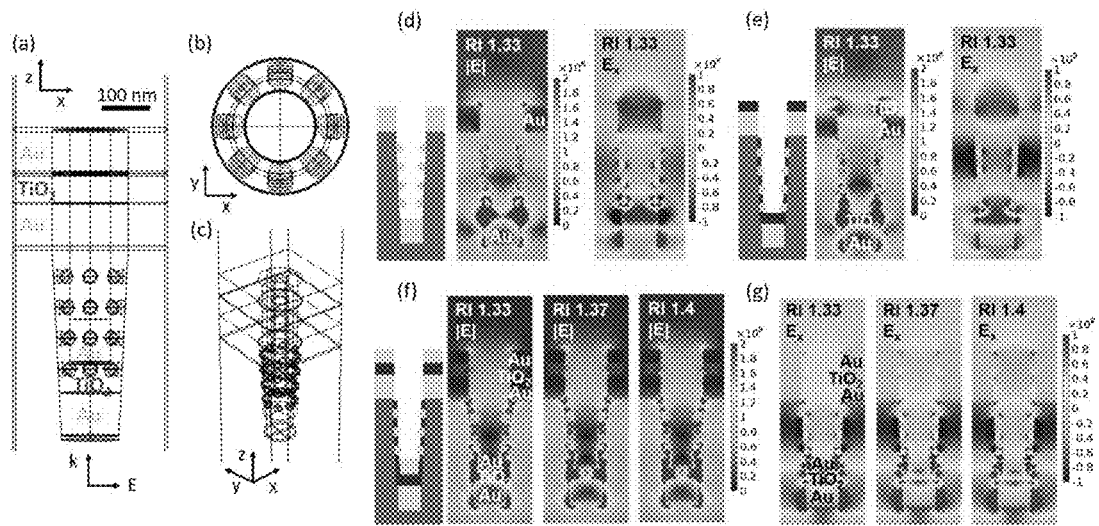
FIG. 2. Simulated near-field electric field distributions shown on resonance for the cross-section of the nanocup device with different Au and titanium dioxide layers. (a) Cross-section schematic of the MIM nanocup 3D-FEM model, which has periodic boundary conditions along x and y. Au nanoparticles are modelled along the cup sidewalls. (b) Top-down schematic and (c) 3D rotated view of the MIM nanocup. |E| and $E_x$ for nanocup with 90 nm Au layer (d) and Au layer with additional 40 nm titanium dioxide layer (e). |E| (f) and $E_x$ (g) near-field electric field distributions are shown for Au-titanium dioxide-Au MIM nanocup with a 50 nm top Au layer with increasing RI values.
Figure 4:
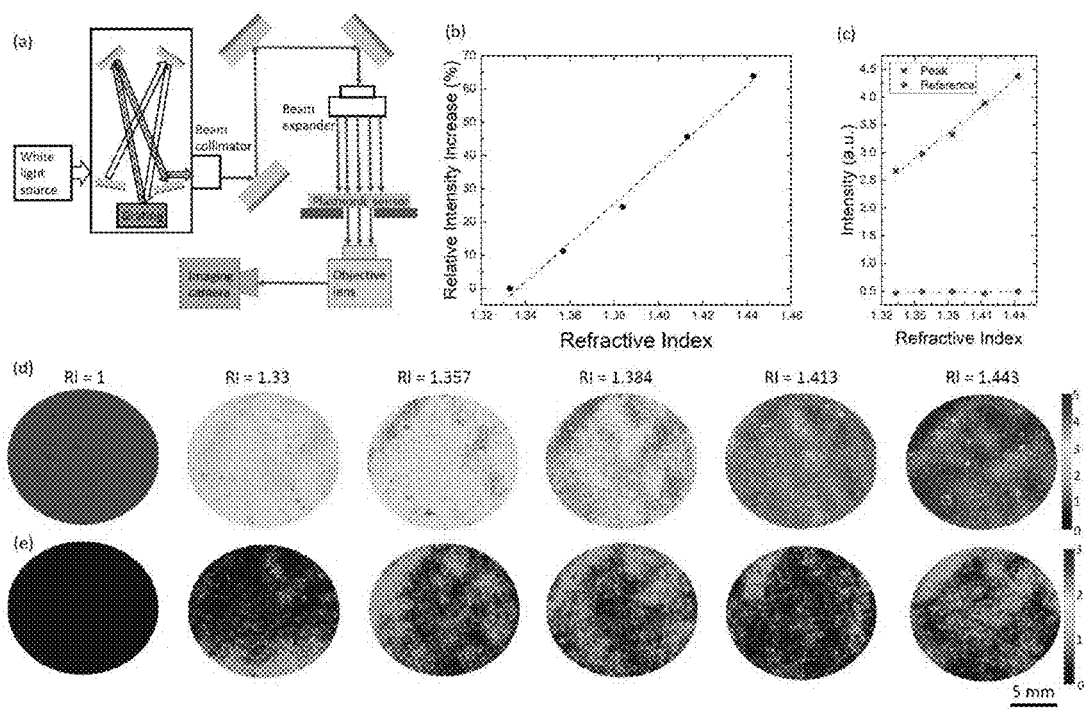
FIG. 4. Spectrometer-free sensing assessment of the MIM nanocup array device. (a) A schematic of the testing setup used for wavelength selection and imaging. (b) Relative intensity increase as a function of refractive index of the superstrate solution. (c) Intensity at the peak (700 nm) and reference (623 nm) wavelengths as a function of refractive index increase. The images of the sensor surface are shown at the peak wavelength (d) and the reference wavelength (e).

Cross-sections of the near-field electric field distributions in the MIM nanocup from the 3D-FEM simulation study are shown in FIG. 2. All the near-field distributions shown are at the transmission resonance wavelength. FIG. 2d shows the normalized electric field (|E|) and the x-component of the electric field ($E_x$) with only a 90 nm bottom Au layer (no insulator and second Au layer). $E_x$ is shown because the incident light in the simulation is polarized along the x-axis. The z-component of the electric field ($E_z$), along the direction of simulated light propagation, is shown in FIG. 9. In FIG. 2d, there is a highly localized field at the bottom of the nanocup, at the rim of the nanocup, and at the Au nanoparticles along the cup sidewalls, which is expected due to the excitation of LSPR resonances in the plasmonic device. FIG. 4e shows the electric field distributions with the addition of a 40 nm titanium dioxide cavity layer. The distributions of highly localized fields remain similar suggesting that the sensor is still primarily operating as a plasmonic device. FIGS. 4f-4g show |E| and $E_x$, respectively, for a MIM plasmonic nanocup array with a 90 nm bottom Au layer, 40 nm titanium dioxide cavity layer, and 50 nm top Au layer with increasing superstrate RI values. With the addition of the top Au layer, there is now a confined mode in the cavity layer at the bottom of the nanocup with high electric field intensity. There is also a localized field near the top of the nanocup that is surrounded by the upper MIM structure. As the RI value of the superstrate increases, there is an increase in the electric field intensity at the top of the nanocup.

The simulation results indicate that the sensing mechanism is primarily driven by the MIM sensor. Light is incident from the bottom of the nanocup and the confined optical energy is stored in the titanium dioxide cavity layer. When there is a RI increase at the superstrate, resonant light is coupled out from the cavity layer to the far field resulting in a transmission intensity increase. While the cavity design is inherently leaky, a sufficient quality factor (Q-factor) is required for the sensor to show a large relative change in transmission with no spectral shift. The role of the plasmonic effect is two-fold. First, the plasmonic properties of the nanostructured Au provide high field localization and confinement. Second, the plasmonic effect will lead to efficient light scattering and out-coupling of the light from the cavity to the far-field such that the performance of this device far exceeds what can be accomplished with a MIM structure without any plasmonic component. Therefore, the Q-factor of the cavity and degree of plasmon-cavity coupling are two crucial parameters for refractometric sensing with this device.

Example 13. Effect of Cavity Thickness

Figure 3:
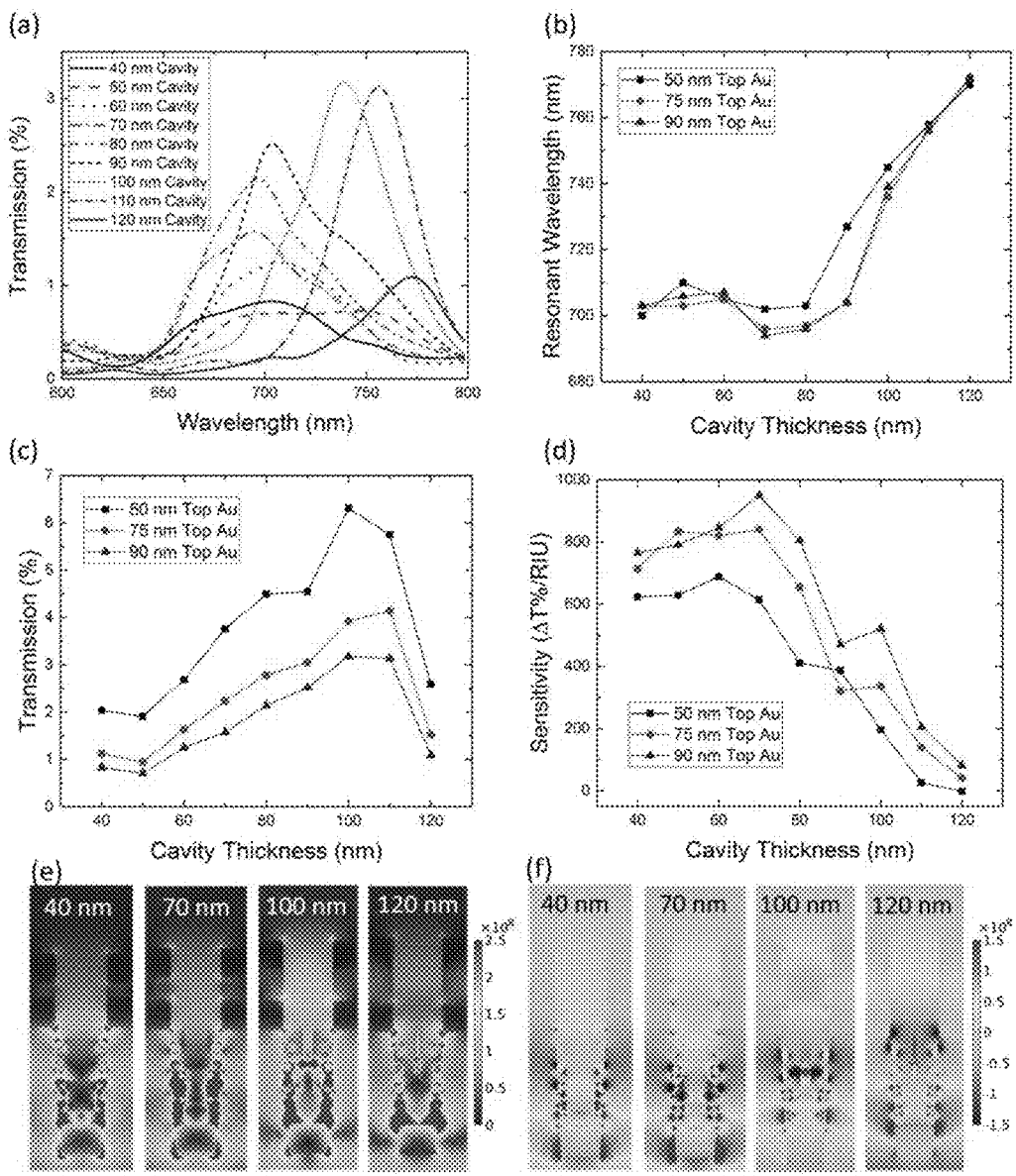
FIG. 3. Simulated spectral and near-field assessment of plasmon-cavity coupling in MIM nanocup arrays. (a) Simulated transmission spectra with increasing titanium dioxide cavity thickness. (b) Resonant wavelength as a function of cavity thickness. (c) Transmission intensity at the peak resonance wavelength as a function of cavity thickness. (d) Refractometric sensitivity as a function of cavity thickness. Near-field electric field distributions |E| (e) and $E_x$ (f) for different cavity thicknesses.

To determine the degree to which cavity-plasmon coupling affects the sensing performance of the MIM nanocup array, the effect of the cavity thickness was modelled. FIG. 3a shows the simulated transmission spectra for the MIM nanocup array with a superstrate RI of 1.33 and changing cavity thickness values from 40 nm to 120 nm with a step size of 10 nm. Spectral changes with increasing top and bottom Au layers are shown in FIGS. 11-12. In FIG. 3a, the bottom and top Au layers were 90 nm. The changing cavity layer thickness results in spectral shifts and changes to the transmission intensity at the peak resonance wavelength. This is shown in FIG. 3b-3c where the resonant wavelength and transmission intensity, respectively, are plotted as a function of the cavity thickness with a bottom Au thickness of 90 nm and a top Au thickness of 50 nm, 75 nm, and 90 nm. The transmission intensity for all top Au layers has a maximum value at a titanium dioxide cavity layer of approximately 100 nm. It is assumed that the transmission maximum will occur when there is optimal overlap and coupling between the cavity resonance and the plasmonic resonance.

In FIG. 3d, the sensitivity is plotted as a function of the cavity thickness. The sensitivity value, here taken from a RI value of 1.33 to 1.34, increases with increasing cavity thickness until it reaches a peak value at a cavity thickness of 70 nm. The sensitivity value then decreases with increasing cavity thickness. At a cavity thickness of 100 nm, the sensitivity is at approximately half of its peak value. This result suggests that to have the optimal sensitivity, a MIM structure should be designed such that the cavity resonance is off of the plasmonic resonance. In particular, the cavity thickness where this doubly resonant condition is approached, but is still off-resonance such that the optimal increase in transmission intensity occurs with RI increase.

This condition can also be understood by the near-field electric field distributions for different cavity thicknesses as shown in FIG. 3e (for |E|) and FIG. 3f (for $E_x$). In these electric field distributions, the top and bottom Au layers are both 90 nm. The field distributions for the 40 nm and 70 nm cavity layers both show the confined mode in the titanium dioxide cavity layer at the bottom of the nanocup. The electric field intensity for this cavity mode is higher for the 70 nm cavity than for the 40 nm cavity, which may be an indication of the higher sensitivity for the thicker cavity layer. Once the cavity layer is 100 nm, the electric field intensity remains high at the bottom of the nanocup, but there is no longer a clearly confined mode in the titanium dioxide cavity layer. The optimal coupling between the cavity mode and the plasmonic mode leads to highly efficient out-coupling to the superstrate, even for low RI values, which makes this device less sensitive for refractometric detection. At a cavity thickness of 120 nm, where the sensitivity is significantly decreased, the near-field electric field distribution shows greatly reduced field confinement. Overall, the refractometric sensitivity is optimized by choosing the cavity thickness such that it allows sufficient optical energy storage. When the device is designed in this way, the RI change will tune the plasmon resonance wavelength and consequently the optical out-coupling from the device will significantly change. Therefore, the sensing occurs by modulating the internal loss of the cavity, which results in a power change without a spectral shift. The cavity should not couple too strongly with the plasmonic mode; otherwise, too much of the light will be out-coupled and not available to contribute towards the sensing mechanism.

Example 14. Cavity Resonance Tuning and Sensitivity in a Planar MIM Sensor

Figure 10:
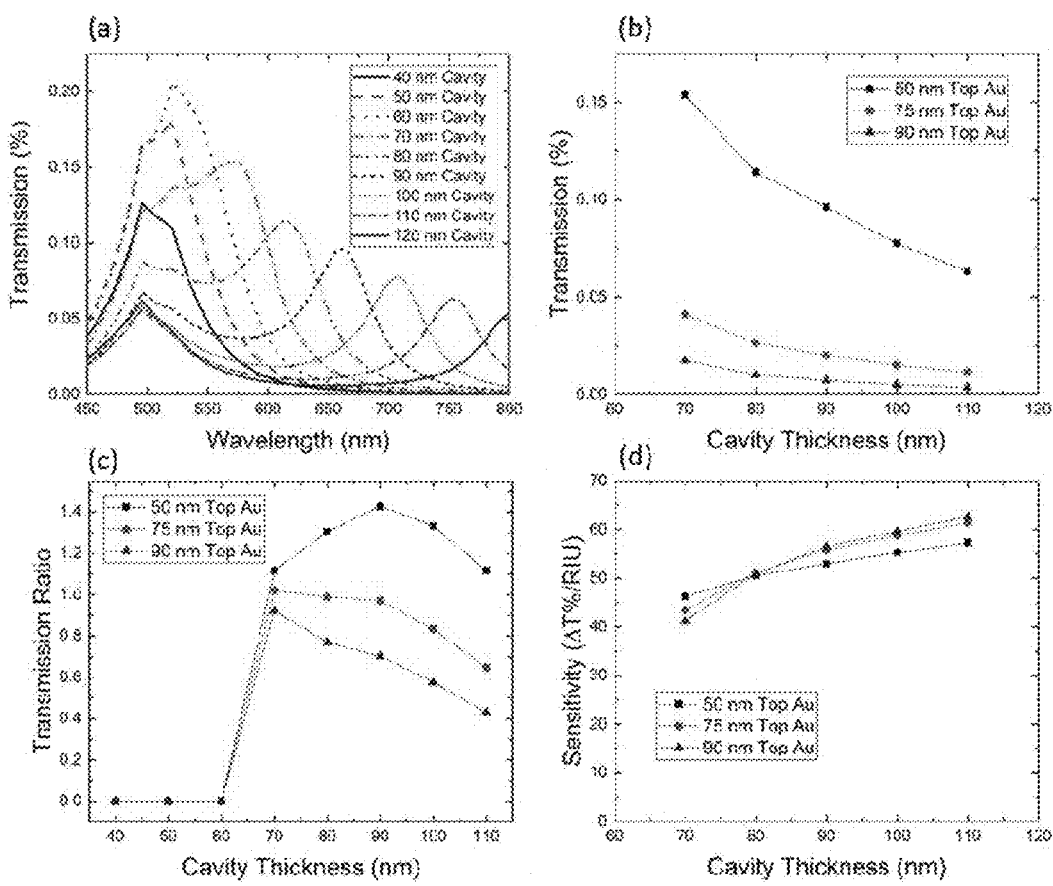
FIG. 10. Cavity thickness dependence in planar MIM sensor. (a) Transmission spectra for increasing titanium dioxide cavity thicknesses. (b) Transmission intensity at the peak cavity resonance wavelength as a function of cavity thickness. (c) Transmission ratio for the cavity resonance and PL resonance as a function of cavity thickness. (d) Refractometric sensitivity as a function of cavity thickness.

Cavity resonance tuning and sensitivity was analyzed in a planar MIM sensor using the TMM with the results shown in FIG. 10, but from the MIM sensor data the same resonance tuning and optimization as for the full 3D-FEM model cannot be recovered since the plasmon-cavity coupling needs to be considered to optimize the device properties. Studies of the properties of the metallic and insulator layers for the full MIM plasmonic nanocup device and the planar MIM sensor alone were also used to investigate plasmon-cavity coupling and the device optimization as described below with results shown in FIGS. 13-14 for the metal material study and FIG. 15 for a study of added loss in the titanium dioxide insulator layer. Overall, it was determined that the optimal materials should be chosen to enhance both the plasmonic and cavity properties of this coupled device to obtain an improved sensitivity value.

Cavity parameter optimization was done by sweeping the top and bottom Au thicknesses and titanium dioxide cavity layer thickness in simulation and experiment to identify the parameters with the largest impact on the device sensitivity. Both the simulation and experimental results, plotted in FIG. 16, suggest that a reliable way to obtain a high device sensitivity is to combine thicker Au layers (higher confinement) with a cavity thickness around 70-80 nm, which will allow the optimal storage of optical energy in the titanium dioxide cavity layer. If the cavity thickness is too large the sensitivity drops significantly as discussed previously. Overall, the device with the highest sensitivity, which exceeds 800 Δ% T/RIU, was obtained for bottom and top Au thicknesses of 90 nm and a cavity layer of 80 nm.

Example 15. Application in Spectrometer-Free Refractometric Detection

The optimized MIM nanocup array device was then assessed for applications in spectrometer-free refractometric detection. The setup utilized is shown in FIG. 4a. A white light source passes through a monochromator, which selects either the peak (700 nm) or reference (623 nm) wavelength. The light at the selected wavelength is then guided through a beam expander and incident on the plasmonic sensor on a sample stage. The light is then collected by a 5× objective lens and goes to an imaging camera. FIG. 4b shows a linear (slope 600±30 and $R^2$=0.99) and consistent relative intensity increase with increasing superstrate RI values from 1.333 to 1.443 from solutions with increasing glycerol concentrations. The increase in intensity at the peak (slope 16±1 and $R^2$=0.99) and reference wavelengths is shown in FIG. 4c and the corresponding transmission intensity images of the device surface are shown in FIG. 4d-4e for the peak and reference wavelengths, respectively. For each intensity image normalization was done with the light source intensity image at 700 nm for the peak image and 623 nm for the reference image. An increase in RI does lead to a consistent and reliable increase in transmission intensity at the resonance wavelength in this spectrometer-free format and the reference spectral location shows good stability with negligible slope.

Figure 5:
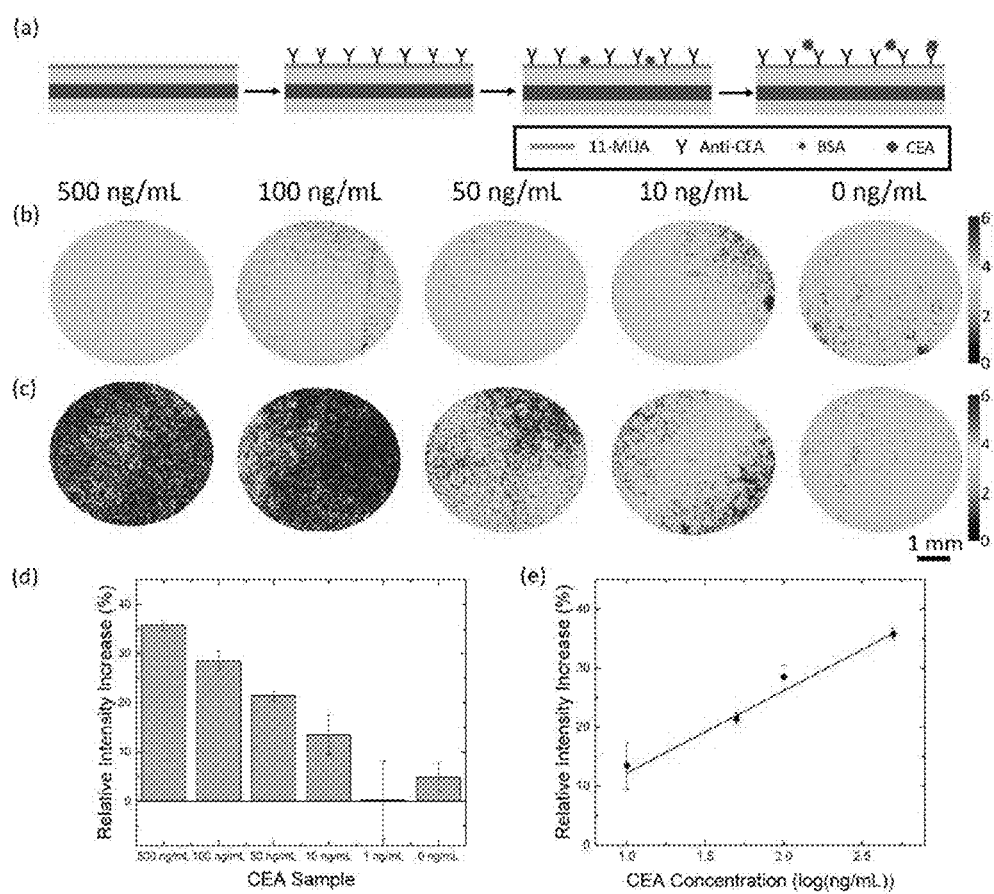
FIG. 5. Spectrometer-free detection of CEA with MIM nanocup arrays. (a) Schematic of anti-CEA immobilization and CEA detection. Images of the sensor surface are shown (b) before and (c) after immersion in CEA solutions with varying concentrations indicated. (d) Relative intensity increase for different CEA samples and (e) relative intensity increase plotted as a function of CEA concentration on a log scale.

Example 16. MIM Nanocup Array and Sensing Method for the Detection of Cancer Biomarker CEA The MIM nanocup array and sensing method were then applied for the detection of the cancer biomarker CEA. The normal concentration of CEA in human serum is 3-5 ng/mL and it becomes elevated (>10 ng/mL) in several cancers, such as breast, lung, and colon, making low concentration detection crucial. A schematic of the CEA detection protocol is shown in FIG. 5a. CEA antibody (anti-CEA, 30 µg/mL) is covalently bound on the Au MIM nanocup surface by 1-ethyl-3-(3-dimethylaminopropyl)carbodiimide (EDC) and N-hydroxysuccinimide (NHS) coupling to an immobilized layer of 11-mercaptuoudecanoic acid (MUA). Nonspecific binding of CEA on the sensor surface is suppressed by two steps. The first is incubation in a bovine serum albumin (BSA) surface blocking agent and the second is immersion in a 10% ethanolamine solution, which caps unreacted NHS. Images of the sensor surface before and after CEA immersion are shown in FIGS. 5b-5c, respectively. To reduce noise, each image represents the peak intensity value (700 nm) divided by the reference intensity value (623 nm) averaged over three relatively defect-free areas (250×300 pixels). The relative intensity increase for the different CEA concentrations studied in this work is shown in FIG. 5d, where the error bar corresponds to the standard deviation for two replicate samples. A LOD of 10 ng/mL is demonstrated with a linear calibration curve ($R^2$=0.98) over a dynamic range of 10 ng/mL-500 ng/mL, as shown in FIG. 5e.

The CEA detection shows that this sensing system can detect protein-protein interactions with a sufficient LOD. The detection of CEA using a commercialized SPR sensing system using a protocol like the one utilized in this work has been previously reported with a label-free LOD of only 100 ng/mL (Altintas et al., Surface plasmon resonance based immunosensor for the detection of the cancer biomarker carcinoembryonic antigen. *Talanta* 2011, 86, 377-383). Therefore, surprisingly the LOD has been improved by an order of magnitude. Therefore, the MIM nanocup array sensor and sensing method presented here are a promising candidate for portable sensing systems.

We claim:

1. An apparatus, comprising:
   a substrate layer having a top surface and a bottom surface, wherein a plurality of nanocups are defined in the substrate layer, wherein the plurality of nanocups each have at least one sidewall surface and a bottom surface;
   a first metal layer disposed on the top surface of the substrate layer and a second metal layer disposed on the bottom surface of each of the plurality of nanocups;
   a first layer of titanium dioxide disposed on the first metal layer disposed on the top surface of the substrate layer and a second layer of titanium dioxide disposed on the second metal layer disposed on the bottom surface of each of the plurality of nanocups;
   a third metal layer disposed on the first layer of titanium dioxide and a fourth metal layer disposed on the second layer of titanium dioxide; and
   a layer of titanium dioxide and a plurality of metal nanoparticles on the at least one sidewall surface of the plurality of nanocups.

2. The apparatus of claim 1, wherein the nanocups have a frustoconical shape.

3. The apparatus of claim 1, wherein the substrate is a polymer.

4. The apparatus of claim 1, wherein the substrate is transparent or translucent.

5. The apparatus of claim 1, wherein the metal layers and metal nanoparticles are gold.

6. The apparatus of claim 1, wherein the metal layers and the metal nanoparticles are a mixture of gold and silver.

7. The apparatus of claim 1, wherein the metal layers and the plurality of metal nanoparticles comprise gold, silver, aluminum, copper, platinum, or alloys thereof.

8. The apparatus of claim 1, wherein the first, second, third, and fourth metal layers are about 50 nm to about 100 nm thick, and wherein the first and second titanium dioxide layers are about 50 nm to about 100 nm thick.

9. The apparatus of claim 1, wherein the first and second metal layers are about 80 nm to about 90 nm thick, and wherein the first and second titanium dioxide layers are about 70 nm to about 80 nm thick.

10. The apparatus of claim 1, wherein the nanocups are about 25 nm to about 1,000 nm deep.

11. The apparatus of claim 1, wherein the nanocups have a top diameter of about 30 nm to about 300 nm and a bottom diameter of about 25 nm to about 295 nm.

12. The apparatus of claim 1, wherein the metal nanoparticles are about 20 nm to about 40 nm in diameter.

13. The apparatus of claim 1, wherein the substrate comprises about 20, 50, 100, 500, 1,000 or more nanocups.

14. The apparatus of claim 1, wherein the plurality of metal nanoparticles are arranged in a discontinuous manner.

15. The apparatus of claim 1, wherein one or more specific binding substances or one or more analytes are present on the at least one sidewall, the bottom surface of the nanocups, or both the at least one sidewall and the bottom surface of the nanocups.

16. The apparatus of claim 1, wherein when light is directed to the surface of the device, a superstrate refractive index increase causes a transmission intensity increase at the peak resonance wavelength and there is no spectral shift at the peak.

17. The apparatus of claim 1, wherein the apparatus comprises spectral regions having no transmission intensity change.

18. A system comprising an apparatus of claim 1, and a white light source or an LED light source.

* * * * *